United States Patent [19]
Lynnworth

[11] Patent Number: 5,159,838
[45] Date of Patent: Nov. 3, 1992

[54] MARGINALLY DISPERSIVE ULTRASONIC WAVEGUIDES

[75] Inventor: Lawrence C. Lynnworth, Waltham, Mass.

[73] Assignee: Panametrics, Inc., Waltham, Mass.

[21] Appl. No.: 385,901

[22] Filed: Jul. 27, 1989

[51] Int. Cl.⁵ ............................................. G01N 29/04
[52] U.S. Cl. ........................................ 73/644; 73/866.5
[58] Field of Search ..................... 73/644, 642, 866.5, 73/DIG. 9, 629, 627, 599, 597

[56] References Cited

U.S. PATENT DOCUMENTS

| | | | |
|---|---|---|---|
| 2,514,080 | 7/1950 | Mason | 73/644 |
| 3,302,044 | 1/1967 | Lynnworth et al. | 73/644 |
| 4,261,197 | 4/1981 | Mansfield | 73/644 |
| 4,461,178 | 7/1984 | Chamuel | 73/599 |
| 4,510,812 | 4/1985 | Feng | 73/644 |
| 4,596,133 | 6/1986 | Smalling et al. | 73/24 |
| 4,893,496 | 1/1990 | Bau et al. | 73/32 A |

OTHER PUBLICATIONS

Tu et al., "Dispersion Of Ultrasonic Pulse Velocity In Cylindrical Rods", *J. Acoust. Soc. AM.*, 27, pp. 550–555 (1955).
Kolsky, "Stress Waves In Solids", *Propagation In Bounded Elastic Media*, p. 59, Eq. 3.60 (1963).
Crecraft, "Launching Ultrasonic Shear Waves Into Solids At Normal Incidence By Pressure Coupling", *J. Sound and Vibr.*, 1(4), pp. 381–387 (Oct. 1964).
Gelles, "Optical-Fiber Ultrasonic Delay Lines", *J. Acoust. Soc. of America*, 39(6), pp. 1111–1119 (1966).
Day and Smith, "Under-Sodium Viewing", *Ultrasonics Symp. Proc.*, IEEE, pp. 191–194 (1973).
Rogers and Miller, "Ultrasonic Level, Temperature, and Density Sensor", *IEEE Trans. Nucl. Sci.*, NS-29(1), pp. 665–668, Feb. 1982.
Lynnworth and Nguyen, "Theory And Measurement Techniques", *NDT Comm.*, 1, pp. 164–174 (1984).
Green, "An Acoustic Technique For Rapid Temperature Distribution Measurement", *J. Acoust. Soc. A.*, 77(2), 759–763 (Feb. 1985).
Nicholson et al., "Waveguides In Medical Ultrasonics: An Experimental Study Of Mode Propagation", W. N. McDicken & T. Anderson, *Ultrasonics*, vol. 27, pp. 101–106, (Mar. 1989).
Frederick, "Ultrasonic Measurement of the Elastic Properties of Polycrystalline Materials at High and Low Temperatures", *Acoust. Soc. of America*, vol. 20, p. 586.
Bell, "The Velocity of Sound in Metals at High Temperatures", *Phil. Mag.* 2 1113 (1957), pp. 1113–1120.

Primary Examiner—Hezron E. Williams
Assistant Examiner—Louis M. Arana
Attorney, Agent, or Firm—Lahive & Cockfield

[57] ABSTRACT

Methods and apparatus for ultrasonically measuring selected physical parameters of a test material or structure are achieved by selecting and configuring waveguides for transmitting extensional, longitudinal, shear, Rayleigh and Lamb waves into media in a marginally dispersive manner. Marginally dispersive transmission is defined by specific criteria of velocity and waveguide diameter. Methods and apparatus for acoustically isolating the waveguides to permit leakage are included, as well as a method of extension to flexural mode conversion to launch flexural waves into a medium.

68 Claims, 23 Drawing Sheets

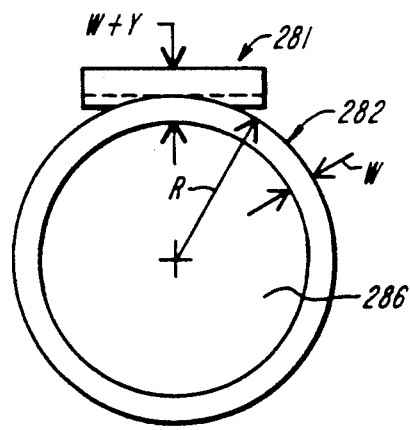
FIG. 28B
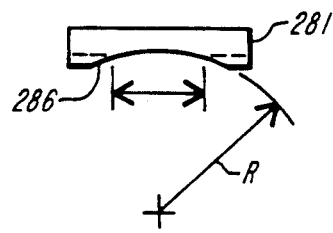
FIG. 28C
| CONDUIT | NOMINAL R, INCHES | NOMINAL W, INCHES | NOMINAL Y, INCHES | W+Y |
|---|---|---|---|---|
| 2" O.D. TUBE | 1.000 | .083 | .292 | .375 |
| 4" SCH 40 | 2.250 | .237 | .138 | .375 |
| 4" SCH 120 | 2.250 | .438 | .062 | .500 |
| 6" SCH 40 | 3.312 | .280 | .095 | .375 |
| 8" SCH 40 | 4.312 | .322 | .053 | .375 |
| 8" SCH 10 | 4.312 | .148 | .227 | .375 |
FIG. 29

| $n$ | $2^n$ | $1/2^n$ | $R_C$ mm* | ISOLATION 10 LOG $2^{-n}$, dB | ISOLATION PER PAIR 20 LOG $2^{-n}$ |
|---|---|---|---|---|---|
| 1 | 2 | .500 | 3 | 3 | 6 |
| 2 | 4 | .250 | 6 | 6 | 12 |
| 3 | 8 | .125 | 9 | 9 | 18 |
| 4 | 16 | .063 | 12 | 12 | 24 |
| 5 | 32 | .031 | 15 | 15 | 30 |
| 6 | 64 | .015 | 18 | 18 | 36 |
| 7 | 128 | .008 | 21 | 21 | 42 |
| 8 | 256 | .004 | 24 | 24 | 48 |
| 9 | 512 | .002 | 27 | 27 | 54 |
| 10 | 1024 | .001 | 30 | 30 | 60 |

*FIG. 35*

MARGINALLY DISPERSIVE ULTRASONIC WAVEGUIDES

BACKGROUND OF THE INVENTION

This invention relates generally to waveguide apparatus and methods, and, more particularly, relates to marginally dispersive ultrasonic energy radiating buffer rods.

Apparatus and methods for non-invasive ultrasonic interrogation and testing of materials and structures have become increasingly significant in a wide range of industrial and scientific settings, including aerospace, automotive, and industrial process control applications. Ultrasonic measurement systems are utilized, for example, in measurement of liquid flow rate in conduits, to detect the presence or level of fluid in containers, for evaluation of material thickness, and for determination of fluid flow velocity, density, or temperature.

Many applications for ultrasonic measurement systems require avoidance of disturbance to the physical process or component to be monitored. Other applications involve aggressive physical environments, such as extreme temperatures or pressures which may pose hazards to transducer materials. In particular, ultrasonic measurements of the properties of solids at elevated temperatures, on the order of 1000 degrees Celsius, is much more difficult than at room temperature, because such temperatures exceed the Curie point of most piezoelectric materials and also exceed the destruction temperature of the couplants commonly used near room temperature.

A variety of techniques and special materials have been proposed or developed to address the problems created by the need for measurements at extreme temperatures. One such solution involves the employment of a buffer rod, or waveguide, which can isolate the transducer from direct exposure to extreme temperatures and thermal shock, and reduce heat transfer from the material to be measured. For example, Frederick, 1948, used a long buffer rod, notched at one end, to separate the specimen from the transducer, permitting speed-of-sound measurement of longitudinal waves in the MHz range in solids at elevated temperature. Subsequently, a number of other investigators employed buffer rods in various forms, including buffer rods which were threaded to suppress spurious echoes due to sidewall reflection and mode conversion. Bell, 1957, employed an elongated buffer rod to convey extensional waves, and later, torsional waves, to and from a small diameter specimen. In Bell's experiments, waveguide diameters were typically between one and a few millimeters, and the selected acoustic frequency was approximately 100 kHz.

Industrial applications, such as steel processing, often require measurement of the propagation of ultrasonic compressional waves, or other ultrasonic waves, through media being processed or stored at extreme temperatures. At high temperatures, signal attenuation due to classical and internal effects is usually much higher than at room temperature. If the media under test are fluids, there may also be considerable turbulence, further increasing the observed attenuation. Past research has demonstrated that interrogation signal frequencies on the order of 100 kHz provide a good compromise between limiting attenuation to a low level, such that sound waves can be propagated efficiently through the test medium, while avoiding the low frequency acoustic background noise often present in industrial operations. The 100 kHz frequency range is accordingly utilized for illustrative purposes in the examples of the invention discussed hereinafter.

For a waveguide that is slender with respect to wavelength, the compressional or extensional wave velocity collectively referred to hereinafter as longitudinal $c_L$ is given by $$c_L = (E/\rho)^{0.5}$$

where E=Young's modulus and $\rho$=waveguide material density. FIG. 1, which depicts wave velocity as a function of waveguide diameter, indicates that, for diameters small compared to wavelength, as the diameter of the waveguide increases, the wave velocity decreases to $$c_L (E/\rho)^{0.5}[1-(\pi\sigma a/\lambda)^2]$$

where d is waveguide diameter, a=d/2, $\lambda$ is wavelength and $\sigma$ is Poisson's ratio. Wave velocity eventually reaches a minimum velocity approximately equal to the Rayleigh velocity $c_R$ at $$a/\lambda = 1 \text{ (approx.)}$$

according to Tu et al., *J. Acoust. Soc. America.* 27, pp. 550-555, (1955).

Waveguide theory predicts that acoustic energy propagating through a waveguide can be dispersive in certain circumstances. In accordance with waveguide theory, when the phase velocity of the components of an acoustic signal is a function of frequency, propagation is said to be dispersive. A pulse or packet of sound waves propagating dispersively will separate into a number of different modes of propagation, each having a different group velocity dependent upon the frequency of the acoustic energy. The number of modes, in turn, depends upon the frequency of sound and the radius of the waveguide. In contrast, in a nondispersive waveguide, sound speed is independent of frequency. The dispersion relation is found in several texts, e.g., Kolsky, *Stress Waves in Solids.* p. 59, Eq. 3.60 (1963). A recent reference on dispersion in both isotropic and anisotropic waveguides is N. C. Nicholson, W. N. McDicken and T. Anderson, in *Ultrasonics* Vol. 27, pp 101-106 (March, 1989).

Tu et al., *J. Acoust. Soc. of America,* 27, pp. 550-555, (1955), indicate that waveguide diameter d must exceed about 5$\lambda$ in order for longitudinal waves to propagate in solids nondispersively. Conventional practice suggests that waveguides for materials testing and process monitoring should be nondispersive to enable precise measurement of signal arrival time, and that dispersive waveguides generate an unacceptable degree of signal "smear" or pulse distortion.

Experiments conducted by Bell, 1957, and Gelles, 1966, to develop nondispersive waveguides, demonstrated that a single buffer rod, or a bundle of thin fibers, respectively, could provide a nondispersive buffer. The fiberacoustic nondispersive bundle is discussed in Gelles, *J. Acoust. Soc. of America* 39 (6), pp. 1111-1119 (1966). Gelles describes a bundle in which the fibers are so slender as to be nondispersive.

However, past attempts to assemble a large number of very slender fibers into a practical probe, for testing red hot steel or other materials having scaled or irregular surfaces, have presented serious technical problems. These difficulties are due to the large number of fibers required for adequate signal transmission, and the low flexural strength of conventional waveguide structures. Ultrasonic measurement systems typical of the prior art do not include elements for pressing fibrous waveguides in a bundle against a test medium, and fail to disclose means for withstanding, without leaking, the pressure of an adjacent fluid at high pressure.

Additionally, certain conventional ultrasonic interrogation systems do not provide elements for resisting waveguide buckling. For example, Rogers and Miller, in *IEEE Trans. Nucl. Sci.* NS-29 (1), pp. 665-668 (February 1982) disclose a stainless steel diaphragm of thickness 50 micrometers—approximately 0.1% of a wavelength—as a low-reflectivity feedthrough penetrated by a welded-in slender waveguide. The Rogers and Miller effort was directed toward determination of liquid level, density and temperature. Their apparatus, utilizing pulse-echo techniques, required highly precise measurement of the time intervals between echoes. These echoes were generated through intentionally introduced discontinuities in the waveguide, rather than in an adjacent medium. By supporting the diaphragm near the waveguide, the unsupported area was kept small, thereby minimizing the force due to hydrostatic pressure. The waveguide itself was suspended vertically and kept straight and in tension by means of a weight element.

The Rogers and Miller apparatus presented no compressive load tending to buckle the waveguide. Waveguide diameter and support elements were therefore not selected or configured to withstand buckling. In accordance with conventional practice, moreover, the cross sectional dimensions of the waveguide were small, compared to wavelength, in order to minimize dispersion. These small cross sections typical of the prior art limit the compressive force which the waveguide can withstand.

The maximum force $F_{max}$ that a 50 micrometer diaphragm of 10 millimeters diameter can support is readily calculated. Assuming a yield strength in be $$(50\ \mu m)(\pi)(10\ mm) = 500(\pi) * 10^{-9} m^2 = 0.002\ in.^2$$

then $$F_{max} = 30,000 * 0.002 = 60\ pounds$$

Thus, while a diaphragm 10 millimeters in diameter can have a 30,000 psi yield strength and can sustain a hydrostatic pressure of nearly 500 psi over its area of approximately 0.125 square inches, it would fail if utilized for applying significant coupling force to a waveguide.

As a numerical example of coupling forces required at room temperature, Crecraft, *J. Sound and Vibr.* 1 (4), pp. 381-387 (October 1964), indicates that approximately 20,000 psi is required to maximize coupling between machined steel surfaces. For a waveguide of diameter d=0.125 inches or about 3 mm, this implies a required coupling force of $$F = (20,000\ psi)(\pi/4)(0.125^2\ in.^2) = 245\ pounds$$

which greatly exceeds the 60 pound limit calculated above for $F_{max}$. Furthermore, a steel waveguide having an unsupported length of at least one foot, and a diameter of 0.125-inch, would buckle at loads far less than 245 pounds, or even 60 pounds.

Conventional waveguide seals and support elements generally do not provide enough structural rigidity for radiating ultrasonic energy from an extensional wave source into fluid media which are at high pressure or into solid media at red hot temperature, which have scaled surfaces, and which accordingly require coupling pressures on the order of thousands of psi or multiple Mpa. (One MPa is approximately equal to 150 psi.)

Moreover, when measuring propagation in media at elevated temperature, the use of longitudinal waves in the MHz range introduces high attenuation, and often requires threading of the buffer rod along most of its length to suppress sidewall echoes. Conversely, conventional application of nondispersive extensional waves in the 100 kHz range implies the utilization of a source diameter at the contact point that is so small as to be inefficient as a radiator in many cases It is thus one object of the invention to provide improved waveguide structures having an efficient aperture for radiating from an ultrasonic wave source into media which are at high pressure or temperature or which require high coupling pressure It is another object of the invention to provide waveguides having enhanced impedance matching and optimum ultrasonic energy transmission into a wide range of test media.

It is a further object of the invention to provide such waveguides which can withstand high coupling pressures without buckling.

Other general and specific objects of the invention will in part be obvious and will in part appear hereinafter.

SUMMARY OF THE INVENTION

The foregoing objects are attained by the invention, which provides methods and apparatus for ultrasonically measuring selected physical parameters of a test material or structure. One aspect of the invention includes selecting and configuring waveguides for transmitting longitudinal, shear, Rayleigh, and Lamb waves into selected media in a marginally dispersive manner. Marginally dispersive transmission is defined herein by the following criteria: c (wave velocity) greater than approximately $0.9(E/p)^{0.5}$; and $(d/\pi)$ less than unity and greater than approximately 0.25, where d is maximum cross-sectional width (hereinafter referred to generally as diameter).

The region of marginally dispersive transmission is further defined by selected values of d sufficiently large that the waveguide does not deflect or droop more than d over its cantilevered length segment $L_c$ between its radiating end and the support nearest that end. Another aspect of the invention provides methods and apparatus for acoustically isolating the waveguides to prevent leakage of acoustic energy around the support structure of the transducer assemblies.

The invention also provides methods and apparatus for launching longitudinal, shear, Rayleigh, and Lamb waves—including lowest-order asymmetric waves—into bulk or plate solids. The waves can be launched from the side or end of marginally dispersive buffer rods. A further aspect of the invention utilizes extensional to flexural mode conversion to launch flexural waves into the medium to be interrogated. A combination of extensional and flexural waves, having selected frequencies, can be generated and received, and the received signals compared, to provide measurement of selected parameters of the material or structure being monitored.

The invention will next be described in connection with certain illustrated embodiments; however, it should be clear to those skilled in the art that various modifications, additions and subtractions can be made without departing from the spirit or scope of the claims.

BRIEF DESCRIPTION OF THE DRAWINGS

For a fuller understanding of the nature and objects of the invention, reference should be made to the following detailed description and the accompanying drawings, in which:

FIGS. 28A–28C depict an embodiment of the invention utilizing a tapered shoe element for contact with a liquid-containing pipe;

FIG. 29 is a chart of shoe dimensions utilized for selected pipe sizes, in connection with the embodiment of FIGS. 28A–28C;

FIG. 35 is a table showing the relationship between the number of noise splitting stages and the degree of isolation provided.

DESCRIPTION OF ILLUSTRATED EMBODIMENTS

Figure 1:
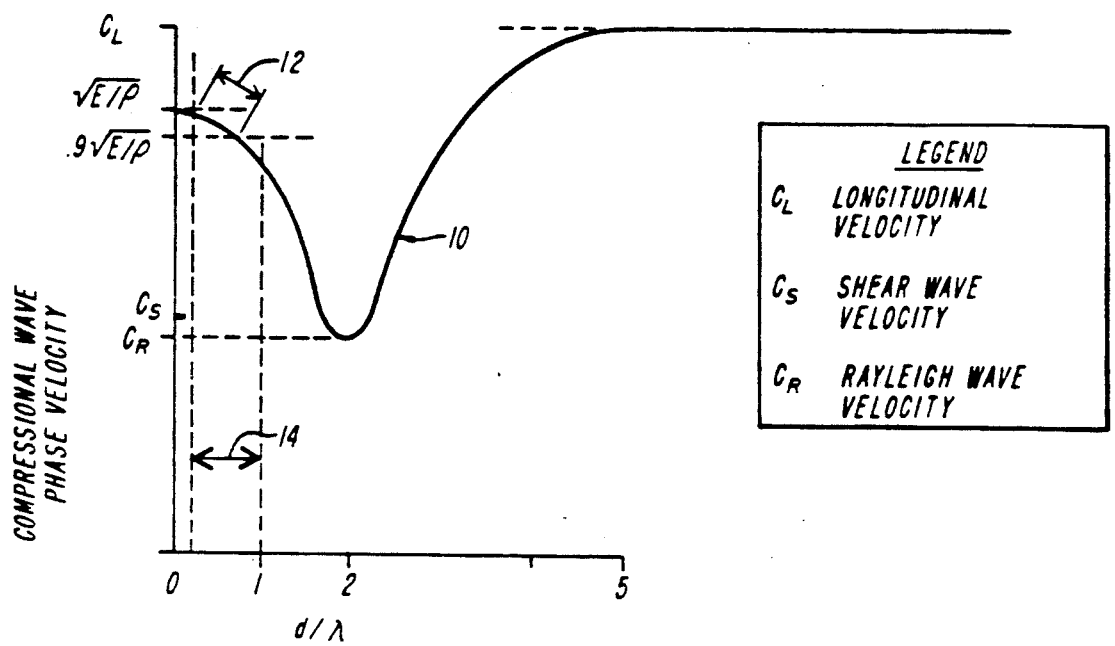
FIG. 1 is an exemplary graph of ultrasonic wave phase velocity as a function of $d/\lambda$.

FIG. 1 depicts an exemplary graph 10 of compressional or extensional wave phase velocity for one value of Poisson's ratio, as a function of the ratio of waveguide diameter d to wavelength $\lambda$. Velocity is indicated with respect to the Y-axis, while diameter-to-wavelength ratio is plotted with respect to the X-axis; The basis of the present invention is to select and utilize waveguides which operate in the marginally dispersive extensional region indicated at 12, to launch extensional, shear, Rayleigh, and Lamb waves —including flexural (lowest-order asymmetric) and other ultrasonic waves.

A preferred practice of the invention utilizes certain selection rules, set forth below with reference to FIG. 1, for configuring waveguides to achieve enhanced transmission of energy and signal/noise ratios superior to those attainable with buffer rods configured in accordance with prior art constraints. For example, when used in ultrasonic measurement of bulk solids, nondispersive/acoustically slender waveguides configured in accordance with the prior art generally suffer from excessive impedance mismatch between waveguide and specimen. As a result, transmission of energy is inefficient, and little energy is radiated into the bulk specimen. If the diameter of the waveguide is increased until it is marginally dispersive, however, the impedance match is much improved.

The marginally dispersive region depicted in FIG. 1 is defined by the following criteria: c (phase velocity) greater than approximately $0.9 (E/\rho)^{0.5}$; and $d/\lambda$ indicated at 14 less than unity and greater than approximately 0.25, where d is waveguide maximum cross-sectional width (hereinafter referred to generally as diameter), $\lambda$ is wavelength, E is Young's Modules and $\rho$ is waveguide material density. This region can be further defined by values of d sufficiently large that the waveguide does not deflect or droop more than a distance d over its cantilevered length segment $L_c$ between its radiating end and the support nearest that end. In this application $\lambda$ is taken to be a characteristic wavelength, for example, the wavelength at the center frequency of a tone burst or pulse.

Moreover, in accordance with the invention, the diameter d can be selected to be small enough, compared to the selected wavelength, so that over most of the waveguide's length the compressional or extensional wave velocity differs from the zero frequency limit by less than 10%, yet large enough so that the droop of horizontal cantilevered segments is less than d. This lower limit on diameter d prevents buckling, ensures that radiation into adjacent transversely unbounded media is reasonably efficient, and provides a waveguide having sufficient extensional wave impedance so that locally-acoustically-massive support or sealing means do not reflect more than 25% of the incident energy.

The curve depicted in FIG. 1 is merely schematic—the exact shape depends in part on the value of Poisson's ratio for the materials selected. In certain embodiments of the invention, described in greater detail hereinafter, the waveguide diameter can be increased, at least locally, to increase the aperture, while not maintaining too large a diameter for too long a distance in the waveguide. The invention is preferably practiced in connection with certain materials in which density and Poisson's ratio are small or in which Young's modulus is large, in order to maximize the aperture while still operating in the marginally dispersive region. Examples of materials having the preferred acoustic properties for a marginally dispersive waveguide are titanium, fused silica, alumina, beryllia and beryllium.

An ultrasonic measurement system constructed to operate in the marginally dispersive region depicted in FIG. 1 at 12 preferably includes elements for acoustically isolating the waveguides. This is because low frequency waves such as the 100 Hz waves preferably utilized in such systems tend to leak around the container or support structure of the transducer assemblies. Acoustic isolation elements, described in greater detail hereinafter, can include dampened concentric tubes joined at one or more points to the waveguide. Isolation elements can also include locally threaded sections on which bushings may be mounted for adapting the slender waveguide to a sturdy concentric supporting tube, or for providing a connection to a flange which is acoustically isolated using gasket materials which attenuate ultrasound.

The invention can be practiced in connection with methods for conically transforming the cross section of a waveguide, over a distance of less than approximately two wavelengths, to a small diameter appropriate for utilizing certain standard small diameter magnetostrictive transduction coil components, or to a slightly larger diameter for utilizing certain radial mode or hoop mode transducers whose diameter may be slightly larger than the preferred diameter for the long buffer. The marginally dispersive waveguide criteria set forth above include extensional waveguides where total transit time along the waveguide exceeds the zero-frequency value by no more than 10%. In other words most of the ultrasonic energy propagates at an average phase velocity in excess of $0.9(E/\rho)^{0.5}$.

Preferred embodiments of the invention include elements for supporting, guiding, mounting, holding or pressing the waveguides against the test medium, for acoustically isolating the waveguide from a fluid test container while maintaining a fluid-tight seal, and for shielding one waveguide from another to prevent acoustic crosstalk. In a preferred practice of the invention, requirements for alignment of a pair of waveguides can be relaxed, because the directivity of the radiation pattern is low to moderate. Threading, tapering, forging or other nonuniform cross section and surface modifications can be employed to adapt marginally dispersive waveguides to a variety of applications in which the medium being interrogated ultrasonically is a fluid or solid at an extreme temperature, high pressure, or is corrosive, hazardous or reactive, or requires high coupling pressure.

As described below in connection with the following examples and equations, the invention can be adapted for particular applications, including liquid level or interface detection, flare gas flow measurement, steam flow and enthalpy measurement, internal and surface temperature distribution in hot workpieces, and sensing the presence or absence of a cryofluid on the remote side of a vessel or tank wall.

It is well known that dispersion complicates the task of obtaining accurate measurement of the time interval for ultrasonic pulses to propagate across one or more paths in a solid, liquid, gaseous, or multiphase medium interrogated ultrasonically, because different frequencies in the pulse travel at different velocities. In accordance with the invention, the compressional or extensional wave of $(E/\rho)^{0.5}$ over at least 75% of the waveguide's length. The marginal dispersion aspect of the invention also requires that the time delay in the acoustic length $L_a$ between the transducer and the radiating end shall not exceed the "zero frequency" delay $$t_o = L_a/(E/\rho)^{0.5}$$

by more than 10%. A third constraint can be imposed for cases where "smearing" is to be kept small, by requiring that $$t_1 - t_o < T/3$$

where $t_1$ = time for the pulse center frequency $f_0$ to propagate over the distance $L_a$, and $T = 1/f_0$.

As a numerical example, let us consider a waveguide material one meter in length, in which Poisson's ratio ($\sigma$) has the value $$\sigma = 1/\pi = 0.3183$$

The phase velocity relation simplifies to $$c = (E/\rho)^{0.5}(1 - a^2/\lambda^2)$$

If $(E/\rho)^{0.5} = 5000$ m/s, then $t_0 = 200$ microseconds and $$1/5000 \ (1-a^2/\lambda^2) = 203 \text{ microseconds}$$

if $a/\lambda = 0.125$. At 100 kHz, T = 10 microseconds and $$t_1 - t_3 = 3 \text{ microseconds} < T/3$$

satisfying the "small smear" constraint. If $a/\lambda$ is doubled to 0.25, c would be reduced by 6.25% from the $(E/\rho)^{0.5}$ value, and $L_a$ would have to be reduced to 0.25 m in order to keep $t_1 - t_0 < T/3$ at 100 kHz. In this 100 kHz example, for wavelengths $\lambda$ of approximately 50 millimeters in the waveguide, the 6.25% dispersion, although probably too large for many pulse measurements in the waveguide itself, permits a diameter d of approximately 25 mm, which is large enough to provide ruggedness, freedom from buckling, and negligible droop up to at least 50% of the waveguide's absolute melting temperature $T_M$.

Additionally, if acoustic radiation is desired into adjacent hot air at, for example, 700° C. (where $c_{air}$ is approximately 625 m/s) the source diameter d is 4 times the wavelength in air—i.e., 4 $\lambda_{air}$. The cone angle $\Theta_3$ dB between 3 dB points of the radiation pattern is therefore approximately $$\lambda_{air}/=\tfrac{1}{4} \text{ radian}$$

or about 14.3°. This radiation pattern may be termed mildly directive, somewhere between that of a nondirective isotropic or simple source and that of a highly directive source having a diameter some 10 or more times the wavelength in the adjacent medium (e.g., a fluid).

The foregoing constraints on phase velocity and time delay, along with $d/\lambda < 1$, further define the upper limits on diameter/wavelength ratio which establish the marginally dispersive region depicted in FIG. 1 at 12. The lower limits on $d/\lambda$ may be varied to suit particular applications, provided $d/\lambda > \tfrac{1}{4}$. The intended function of the waveguide, in turn, partly determines the material (e.g., steel or ceramic) and geometry (such as circular cross section or noncircular cross section) to be utilized for the waveguide. For noncircular cross sections d is defined herein as the major diameter of the longest segment, unless stated otherwise.

In accordance with the invention, a lower limit for waveguide diameter d can be selected with reference to wavelength and required waveguide stiffness. Because deflection varies inversely with stiffness (E) and nonlinearly with d, while $\lambda$ varies primarily as (E) 0.5, selection rules for $d/\lambda$ based on droop are material- and shape-dependent. If wind forces and vortex-shedding-induced vibrations are to be withstood without failure, the selection rules become more complex. For simplicity, one practice of the invention utilizes a lower limit for d such that buckling is unlikely, and such that the droop of the cantilevered segment length $L_c$ between the radiating end and the nearest support would be less than d.

Moreover, in view of the mechanical strength requirements of typical applications anticipated for the invention, d should be large enough so that, if in compression, the waveguide will not buckle at a load of 100 kg or at the actual load, whichever is less. High-modulus cantilevered waveguides can satisfy the small-droop constraint at a smaller d than can low-modulus waveguides.

FIGS. 2-24 illustrate preferred embodiments in which these d and $d/\lambda$ constraints are satisfied in waveguide configurations that provide enhanced measurement of the properties and characteristics of solids, fluids, and multiphase media. In the following examples, temperature, fluid flow rate, material thickness, and other parameters are measured through ultrasound propagation in the media under test, or in their container, or in a sensor immersed in the medium whose parameters are to be determined. The ultrasound is typically transmitted from and/or received by marginally dispersive waveguides constructed in accordance with the invention. In particular, the real part and/or the imaginary component of the acoustic or ultrasound propagation data can be interpreted in a known manner in terms of one or more measurands of interest, such as temperature, flow, interface location, composition, or material state. Electronic instruments for making such measurements, when operated in conjunction with the waveguides herein, are well known in the art.

Moreover, waveguides constructed in accordance with the invention may be utilized to launch longitudinal, shear, Rayleigh, or Lamb waves—including flexural waves— depending upon the medium and measurand of interest. The following table summarizes the transmission modes of marginally dispersive waveguides constructed in accordance with the invention.

TABLE I

| Summary of Marginally Dispersive Transmission Modes | | |
|---|---|---|
| Medium | Interrogating Wave | Launched From |
| Fluids: | | |
| Gases | Longitudinal | Waveguide end or side |
| Liquids | Longitudinal | Waveguide end or side, or by mode conversion at interface with solid |
| Solids: | | |
| Bulk | Longitudinal Shear, Rayleigh | Waveguide end |
| Plate | Longitudinal, Shear, Rayleigh, Lamb, including flexural, the lowest-order asymmetric plate wave | Waveguide end |

Utilization of the flexural wave launched by a marginally dispersive waveguide, for example, has many potential applications. Flexural-mode-based applications include measurement of red hot steel tubing wall thickness, detection of the presence of automotive fluid such as transmission oil at a particular level in a torque converter —where the housing is of irregular contour and surface as to prevent successful measurement by conventional ultrasonic methods—, location of foam interface in an industrial separator, and measurement of the flow of water (single and two phase) in thin-walled pipe.

Most ultrasonic thickness measurements in industry today are obtained by using longitudinal waves at normal incidence. However, at temperatures near 1000 degrees Celsius —the approximate temperature of red hot steel— longitudinal transducers and components are generally unsuitable. One alternative, discussed in greater detail below, is to employ flexural waves coupled via extensional mode buffers and point or chisel contacts to the hot workpiece. Measurement of material thickness is based on the thickness dependence of the phase velocity $c_f$ of flexural waves at low frequency.

Flexural waves propagating in a plate resemble the ripples traveling in a wavy flag. In the class of waves referred to as Lamb waves (also referred to as plate waves), the flexural wave is the lowest-order asymmetric mode, $a_0$. For f*d products (frequency-plate thickness) somewhat less than approximately one MHz-millimeter, the phase velocity $c_f$ of this plate mode, for the plate surrounded by vacuum, depends on the plate's elastic properties —Young's modulus E, density $\rho$, Poisson's ratio $\sigma = E/2G - 1$ where G is the modulus of rigidity for the material and the square root of the f*d product, as follows:

$$c_f[E/12\rho(1-\sigma^2)]^{\frac{1}{4}}[2\pi f d]^{\frac{1}{2}}$$

Flexural waves are of interest because they can radiate into adjacent fluids in which the sound speed is less than $c_f$, and their propagation in the plate, i.e., in the container wall, responds to the fluid adjacent the wall, i.e., its presence, density and thickness. The value of $c_f$ decreases significantly when one or both surfaces of the plate are immersed, depending on fluid density and the thickness of the adjacent liquid layer, and on the plate's thickness and elastic properties. Flexural waves can be launched by mode conversion, such as by conversion from extensional waves. Table II, set forth below, summarizes selected applications of mode conversion of extensional to flexural waves.

TABLE II

| Mode Conversion of Extensional to Flexural Waves | | |
|---|---|---|
| Source of 100 kHz extensional waves | Converted in a thin-walled plate or vessel to | Flexural wave responsive to |
| Magnetostrictive or piezoelectric transducer | Flexural | Plate properties, thickness Presence/absence of liquid Liquid density Liquid thickness Liquid/vapor interface location |

These applications will be discussed in greater detail below. In particular, among the embodiments of the invention depicted in FIGS. 2-24 are systems utilizing mode conversion for launching flexural waves for measurement of material or structural properties.

Figure 2:
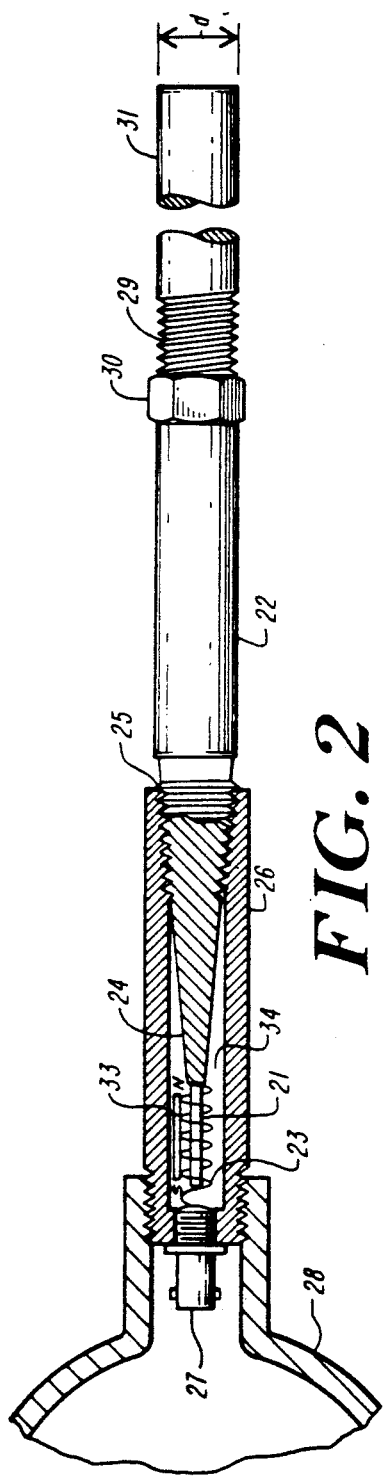
FIG. 2 illustrates a magnetostrictive transducer and marginally dispersive waveguide constructed in accordance with the invention.

FIG. 2 shows a magnetostrictive transducer 21 and marginally dispersive waveguide 22 in accordance with the invention. A coil 23, grounded at one end in combination with magnet 33, excites ultrasonic pulses, which can be at frequencies on the order of 100 kHz, in the magnetostrictive segment 21. Segment 21 can be a stub, 25 millimeters in length and 1.6 millimeters diameter, of Remendur alloy —approximately 49% iron, 49% cobalt, and the remainder manganese and vanadium. This stub can be brazed into a small hole drilled in the conical end 24 of waveguide 22. A suitable material for waveguide 22 is stainless steel. Near the thickest part 25 of the cone a tapered pipe thread mates with and seals sleeve 26. Sleeve 26 can also hold an electrical connector 27 and can be threaded into an explosion-proof junction box 28. Returning to waveguide 22, its cylindrical portion can include another tapered pipe thread 29 and a hex head pattern 30 for screwing it leak-tight into a pipe or other vessel.

Extending away from the transducer end is the radiating portion 31 of diameter d. Portion 31 may be straight, bent, or curved as shown at 32. The cost of the Remendur stub 21 can be limited by utilizing a small diameter. The embodiment shown in FIG. 2 can utilize standard parts for the stub 21, coil 23 and magnet 33— whose north (N) and south (S) ends line up with the coil ends. The coil 23 and magnet 33 can be potted with ordinary or high-temperature potting materials 34, such as General Electric Corporation's Triplus ™ solventless silicone resin or Theramic Engineering, Inc.'s types 900, 1000, or other ceramic adhesives currently supplied from their Waterford, N.Y., and Miami, Fla., locations respectively. The magnetostrictive stub 21 alternatively may be a composite such as epoxy-filled nickel tubing (to achieve a lower sound speed, lower-frequency transducer for a given length transduction region) or nickel plated alumina (to achieve a higher sound speed and higher-frequency transducer).

Figure 3:
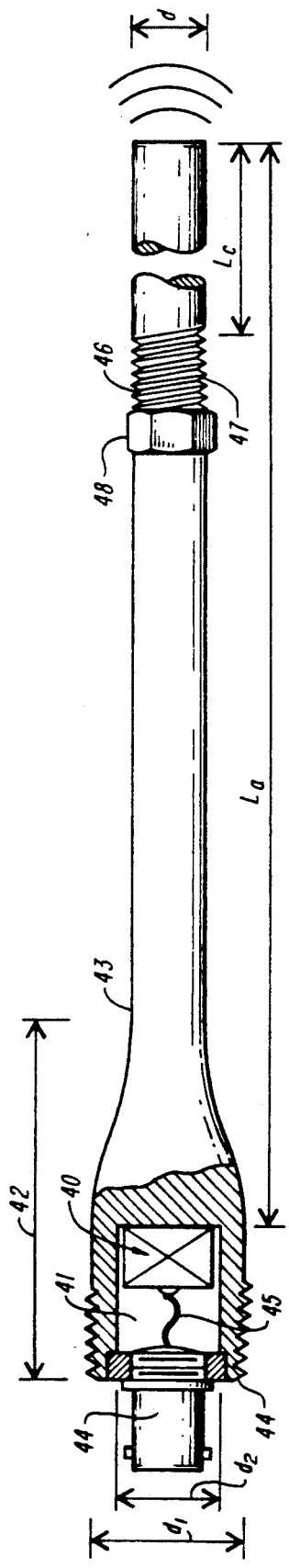
FIG. 3 depicts a piezoelectric transducer and marginally dispersive waveguide according to the invention.

In FIG. 3 a piezoelectric radial mode 100-kHz transducer 40 is bonded in the cavity 41 in the enlarged end 42 of waveguide 43. Transducer 40 is attached to electrical connector 44 via lead wire 45. Experiments conducted with this design utilized aluminum and subsequently titanium rods of 12.7-millimeters diameter (d) over most of the rod length The diameter was enlarged to 21.3 millimeters ($d_1$) to accommodate a standard ½-inch pipe thread 44, and bored to 17.4-millimeters inside diameter ($d_2$) to accommodate a standard 100-kHz radial mode piezoelectric transducer 40 of 15.9-millimeters diameter. The enlarged outside diameter region 42 can be between d and 2d in length, as is the other enlarged region 46 containing a ⅜-inch pipe thread 47 and hex nut pattern 48.

Figure 4:
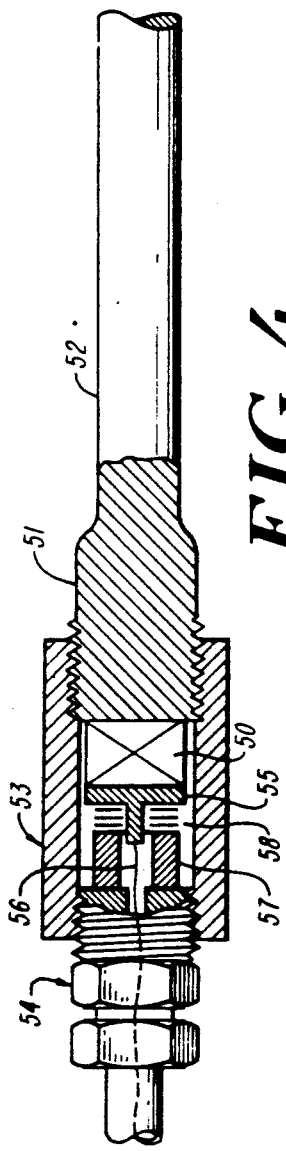
FIG. 4 illustrates one method of pressure coupling a piezoelectric transducer to a marginally dispersive waveguide.

FIG. 4 shows an alternate method for attaching a piezoelectric transducer to a marginally dispersive waveguide. In FIG. 4 transducer 50 is pressure coupled to the enlarged end 51 of waveguide 52. A standard pipe coupling 53 and a standard male pipe connector 54 are used to exert a coupling force on transducer 50 and enlarged end 51 through pressure pad 57 and electrical insulator 58. Transducer 50 is electrically connected to control circuitry (not shown) via electrode 55 and lead wire 56.

Figure 5:
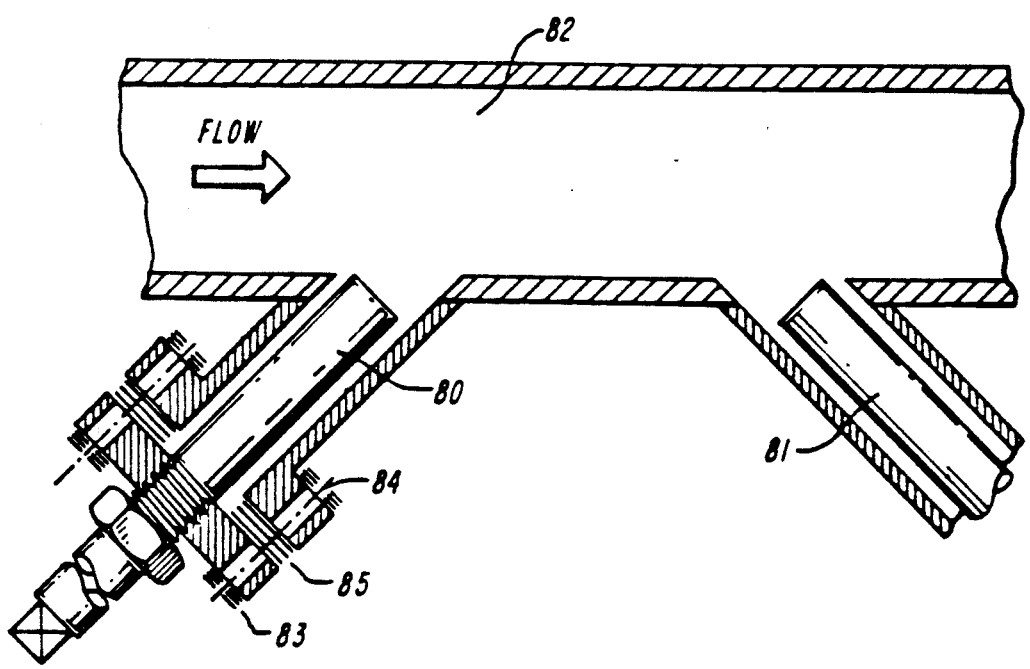
FIG. 5 shows a configuration utilizing a marginally dispersive waveguide in accordance with the invention for measuring parameters of steam at high temperature and pressure.

FIG. 5 shows an embodiment of similar radiating waveguides 80 and 81 for measuring flow velocity V, quality Q, enthalpy H, and mass flow rate M of steam at high temperature (approximately 250° C.) and high pressure (approximately 30 bar or 3 MPa) contained in pipe 82. The velocity V and sound speed c in the steam, are directly determined by ultrasonic measurements, from which the other measurands can be calculated using additional data such as gas temperature and pressure. An important feature of the embodiment depicted in FIG. 5 is the use of acoustic isolation. Such isolation is useful because low frequency ultrasound, such as the 100 kHz waves preferably utilized in such systems, tend to leak around the container or support structure of the transducer assemblies. This isolation can consist of hard, nonabsorbent, acoustically-dissimilar elements deployed as alternating layers of low-impedance, high-impedance material. For example, the washers 83 and sleeves 84 may consist of mica and steel shims separated by an asbestos substitute such as Klinger® Sil Style C-81 nitrile rubber bonded material made by Klinger, Inc. of Sidney OH. The steel may be roughened to trap air between layers. The gasket 85 may be an asbestos-free Flexitallic gasket, available commercially. The arrangement in FIG. 5 was originally designed for experiments on a steel pipe 82 of 4-inch nominal diameter, schedule 40, bored through at 45° in two places and fitted with welded-on scooped couplings and flanges.

Figure 6:
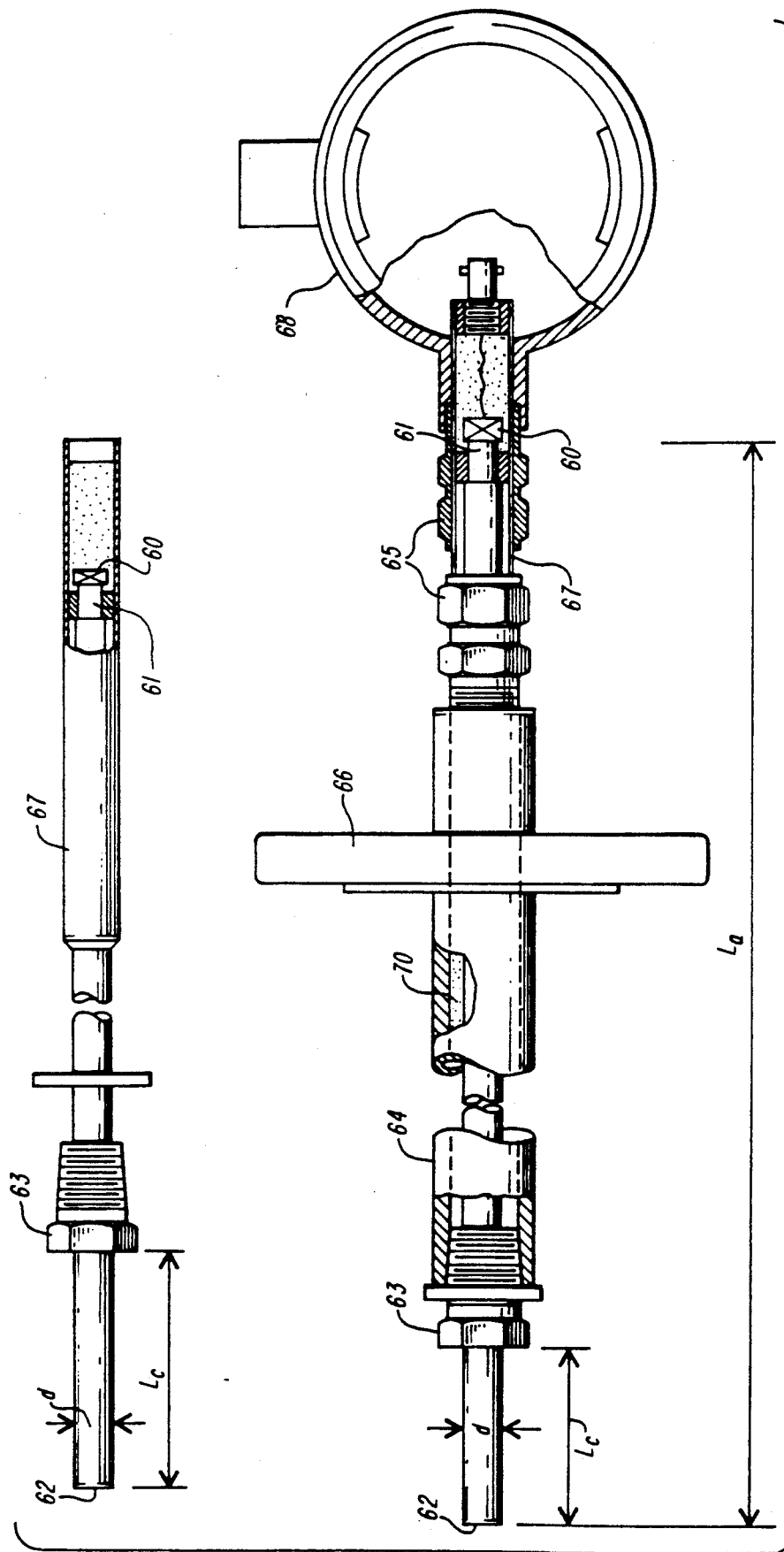
FIG. 6 depicts an embodiment of the present invention intended for flare gas flowmeter applications.
Figure 7A:
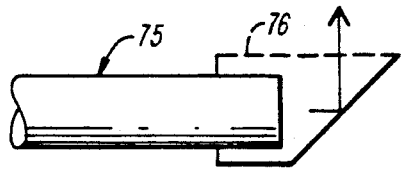
FIGS. 7A–H depicts various ways in which the radiating end of a marginally dispersive waveguide may be modified to aim the center of an ultrasound beam in a particular direction.
Figure 7B:
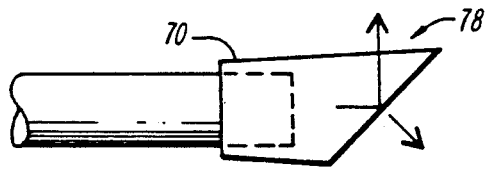
Figure 7C:
Figure 7D:
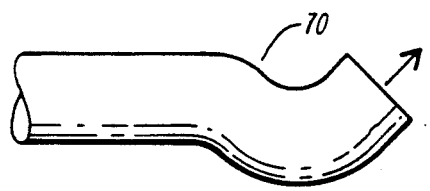
Figure 7E:
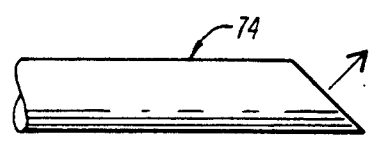
Figure 7F:
Figure 7G:
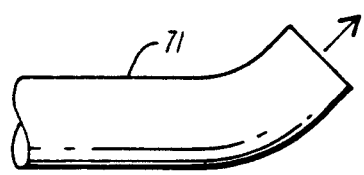
Figure 7H:
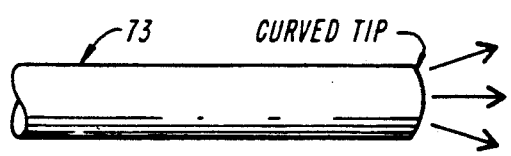

FIG. 6 shows designs intended for flare gas flowmeter applications like those described in commonly-owned U.S. Pat. No. 4,596,133, as well as higher-temperature flare gas applications. In accordance with the invention, the objectives important to high temperature flare measurements are to isolate the transducer from the high temperature region, and to segregate all electrical connections outside the flare gas pressure boundary. A configuration utilizing "straight" acoustic radiation will be described, followed by examples in which the sound beam is preferentially directed into the medium, obliquely or orthogonally with respect to the main axis of the waveguide. One significant feature of the embodiment of FIG. 5 is the use of a sturdy concentric steel tube to securely support the marginally dispersive waveguide of small $d/\lambda$ without overly attenuating the acoustic wave in the waveguide. Another feature is the employment of standard parts welded to the waveguide, so that locally-enlarged areas for support can be provided economically, without requiring an expensive large-diameter rod to be turned down over most of its length merely to retain two support regions.

As depicted in FIG. 6, a piezoelectric crystal 60, which typically resonates near 100 kHz, is attached to waveguide 61. Near the opposite end a distance $L_c$ from the radiating tip 62 there is welded a ⅜-inch bored-through pipe plug 63. Distance $L_c$ may be approximately 100 to 125 millimeters and diameter d can be approximately 12.7 mm. Waveguide 61 and plug 63 are typically constructed from titanium. Sleeve 64 can be SS316 pipe, 1-inch schedule 80, internally pipe-tapped ⅜-inch NPT at opposing ends to accommodate plug 63 and bored-through male pipe connector 65 such as Swagelok's part number SS-810-1-12. Concentric sleeve 64 can be 19-millimeter outside diameter titanium tubing, 1.6-millimeters thickness, welded at one or both ends to waveguide 61. Sleeve 64 can slide through connector 66 until connector 66 is tightened, capturing the sleeve by a conventional swaged ferrule 71. FIG. 6 shows sleeve 64 welded perpendicular to flange 69. This assembly can be mated with a packing gland 70 of conventional design. Another sleeve 67 can be welded or otherwise attached to waveguide 61 or sleeve 64 to create a cavity surrounding piezoelectric crystal 60, providing a means for connecting junction box 68.

In the example illustrated, $L_c$ is drawn intentionally much shorter than the end to end acoustic length La between the crystal 60 and the radiating tip of diameter d. For example, La may be as long as one meter, with $L_c$ being approximately 0.1 meter. In the present example, the ratio of waveguide to sleeve cross-sectional area is $A_{61}/A_{64}$ equal to $(12.7^2)/(19^2-15.8^2)$ equals 1.45. Therefore, mechanical connections to sleeve 64 have relatively little effect on propagation between the crystal 60 and the radiating tip 62, since most of the ultrasonic energy is confined to the waveguide 61.

Although d is not large enough to be highly directive at 100 kHz in flare gases of low molecular weight, it nevertheless can be desirable to aim the center of the ultrasound beam in a particular direction, typically 45° or 90° to the main axis of the waveguide. If a preferred direction of radiation is desired, the end of waveguide 61 may be chamfered, bent, curved, forged or otherwise recontoured, or an additional element may be affixed to its end by mechanical, metallurgical or other means.

FIG. 7 shows examples of alternative embodiments for aiming the ultrasound beam in a preferred direction. Various embodiments utilizing curved waveguide ends are shown at 72, 73, and 74. 75 and 76 illustrate the usage of a chamford radiating tip to direct the ultrasound wave. In another embodiment, a reflectional element 78 is affixed to a basic radiating end 77 to direct the ultrasound wave orthogonally from the longitudinal axis 83 of the radiating end 77. Similarly, directional element 81 may be attached to a basic radiating end 80 to deflect the ultrasound wave from the axis of the radiating end at any one of a plurality of desired angles. Additionally, aerodynamic shields such as shown at 82 which do not alter the direction of ultrasound wave transmission may also be employed.

Figure 8A:
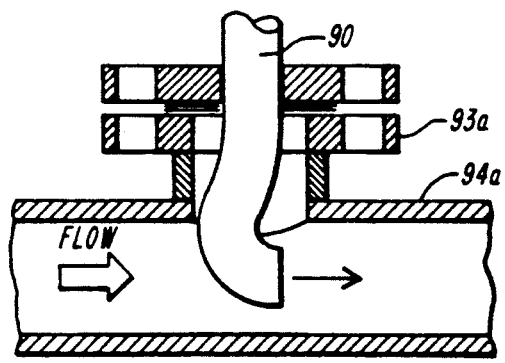
FIGS. 8A–C depicts alternative embodiments of curved selectively dispersive waveguide configurations for flare gas flowmeter applications.
Figure 8B:
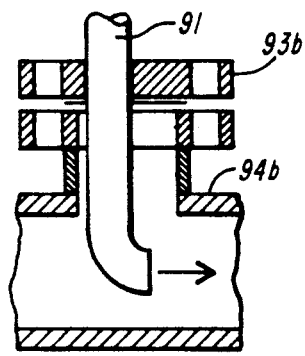
Figure 8C:
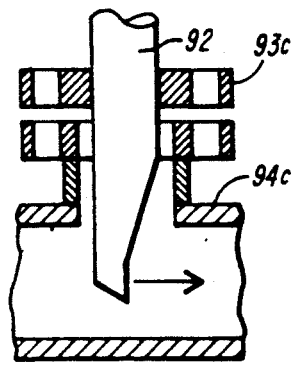

FIG. 8 shows three ways, 90, 91, and 92 including concentric and eccentric, that marginally dispersive waveguides can be curved before or after passing through a flange shown at 93A-93C mounted on a side port of a pipe 94A-94C. A typical application of these embodiments would be to measure sound speed and flow velocity of single-phase or multiphase fluids, including cryogenic fluids subject to flashing.

Figure 9:
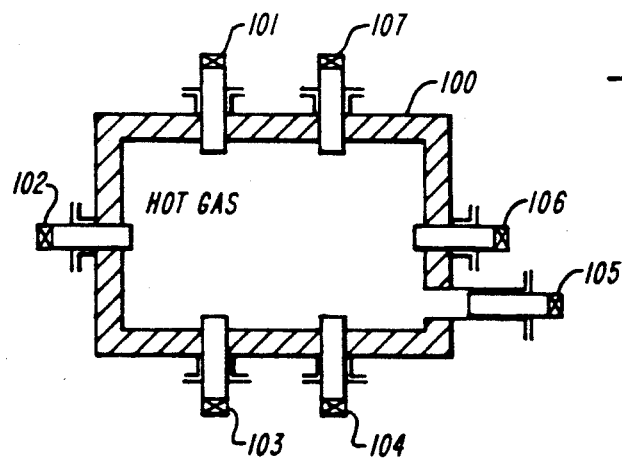
FIG. 9 illustrates various marginally dispersive waveguide installations in a chamber containing hot gases.

FIG. 9 depicts marginally dispersive waveguide installations in a chamber 100 containing hot gases. The multiple interrogation paths depicted in FIG. 9 at 101-107 may be required for mapping the profiles of sound speed in the gas. Temperature distribution can be derived from sound speed, by methods similar to those reported by Green in *J. Acoust. Soc. Am.* 77 (2), pp. 759-763 (February 1985). If a large temperature gradient exists along the waveguide, it is necessary to correct the total transit time t for the delays in both waveguides using a pulse-echo correction formula.

Figure 10:
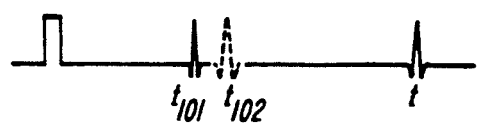
FIG. 10 is a simplified graphical representation of a received waveform which may be generated in connection with the embodiment of FIG. 9.

FIG. 10 depicts the received waveform which may be generated by the embodiment of FIG. 9. Referring to FIG. 10, if the round-trip times in a pair of communicating waveguides 101 and 102 are $t_{101}$ and $t_{102}$, then $$t_{gas} = t - 0.5(t_{101} + t_{102})$$

If the waveguides are constructed of graphite, fused silica, or a ceramic, sound speed will be substantially unchanged even for temperature ranges of 1000° C, thereby possibly avoiding the need for a pulse-echo correction algorithm. However, installation and support of brittle materials —such as fused silica or ceramic— is more complex than that required for metals.

Figure 11:
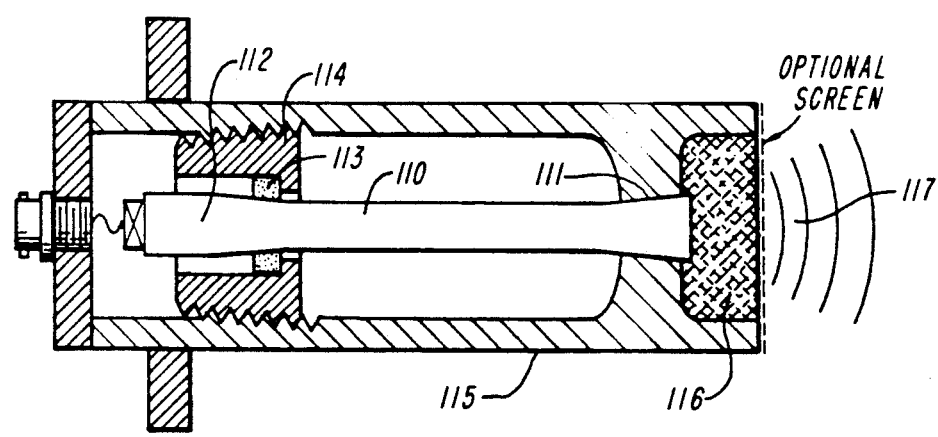
FIG. 11 is an expanded view of one waveguide installation of the type depicted in FIG. 9.

FIG. 11 is an expanded view of one waveguide installation of the type depicted in FIG. 9 and is illustrative of one support technique that avoids the need for threading the waveguide. As depicted therein, a fused silica waveguide 110 is oppositely tapered in two separate locations 111 and 112. A split gasket 113 between threaded ring 114 and the tapered end 112 provides a cushioned support as ring 114 is turned within sleeve 115 thereby securing the waveguide 110. FIG. 11 also depicts low-density loosely-packed fibrous refractory heatshielding material 116 that is retained by screens or other conventional means between the radiating end 111 of the waveguide 110 and the hot gas 117. We have found that even several centimeters of such fibrous material is fairly transmissive to ultrasound, at frequencies as high as 100 kHz.

Figure 12:
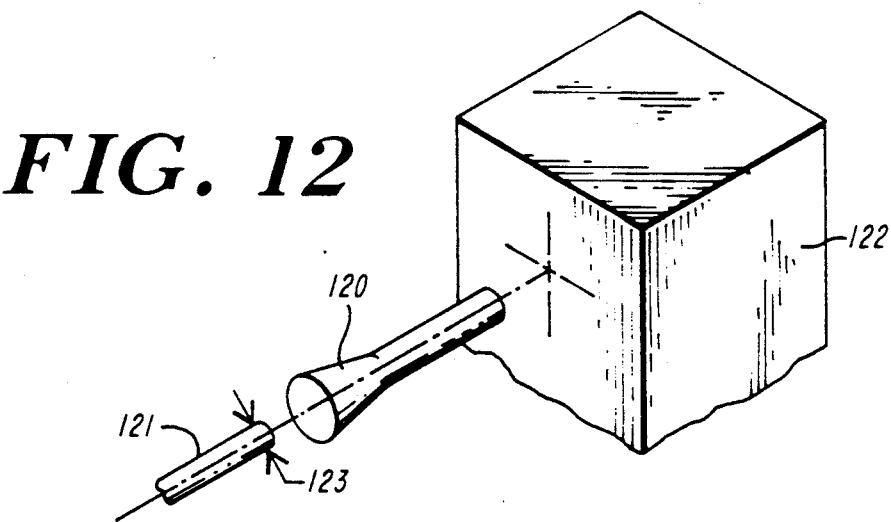
FIG. 12 depicts a waveguide apparatus constructed in accordance with the invention for the measurement of internal and surface temperature distribution of high temperature workpieces.

FIG. 12 depicts an embodiment of the invention for measurement of internal and surface temperature distribution of hot workpieces such as red hot steel billets. A guide element 120 assists in positioning waveguide 121 in the proper orientation against the hot workpiece 122. Laboratory experiments at room temperature have demonstrated that the amplitude of 100-kHz pulses transmitted through relatively large steel workpieces increases as waveguide diameter 123 increases. This may be explained by treating the impedance of the workpiece as if it exhibited an extensional wave load impedance $$Z_L = \rho c A$$

where A is approximately equal to $\pi \lambda^2$. To the extent that the expression $\rho c \pi \lambda^2$ accurately represents $Z_L$, it is recognized that transmission from an extensional mode steel waveguide into the workpiece will increase as diameter 123 approaches $\lambda$. The waveguide of FIG. 12 can be constructed to resemble the waveguide depicted in FIG. 3.

Figure 13:
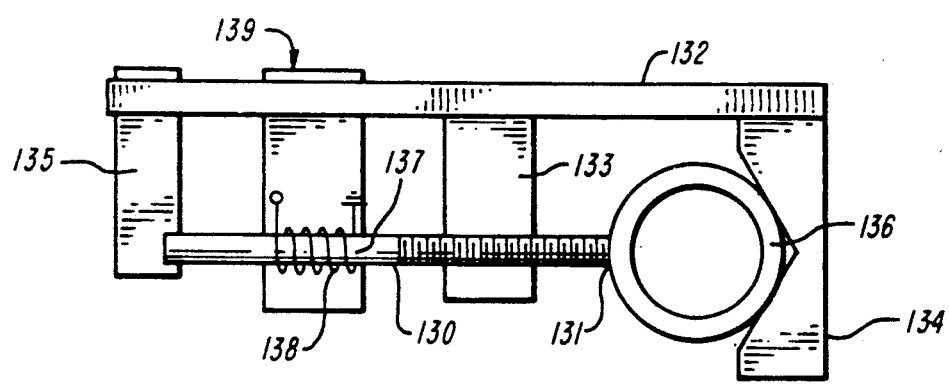
FIG. 13 shows a waveguide apparatus of the type depicted in FIG. 12 wherein pressure coupling is achieved through utilizing a threaded waveguide.

FIG. 13 shows an alternate embodiment of a waveguide apparatus of the type depicted in FIG. 12 wherein the waveguide may be threaded so that, when driven like a leadscrew, pressure coupling may be obtained. FIG. 13 shows a threaded waveguide 130, having radiating end 131, supportingly connected to frame 132 through splint nut 133. Frame 132 also supports a mechanical stop 134. A drive mechanism 135, such as an electrical motor, rotates waveguide 130 through splint nut 133 so as to clamp workpiece 136 between radiating end 131 and mechanical stop 134. A pressure coupling between radiating end 131 and workpiece 136 is thereby achieved. A typical workpiece 136 may be a pipe billet. FIG. 13 also shows the magnetostrictive section 137 of waveguide 130, including coil 138 and transducer assembly 139.

This method is analogous to the coupling methods described or cited by Lynnworth and Nguyen in *NDT Comm.* 1, pp. 164-174 (1984)., except that in the embodiment depicted in FIG. 12, workpiece 136 has cross sectional dimensions on the order of centimeters to tens of centimeters, rather than millimeters —thus, too large to be considered a waveguide for 100-kHz extensional waves— and the temperature of some of the anticipated applications is on the order of 1000° C.

Figure 14:
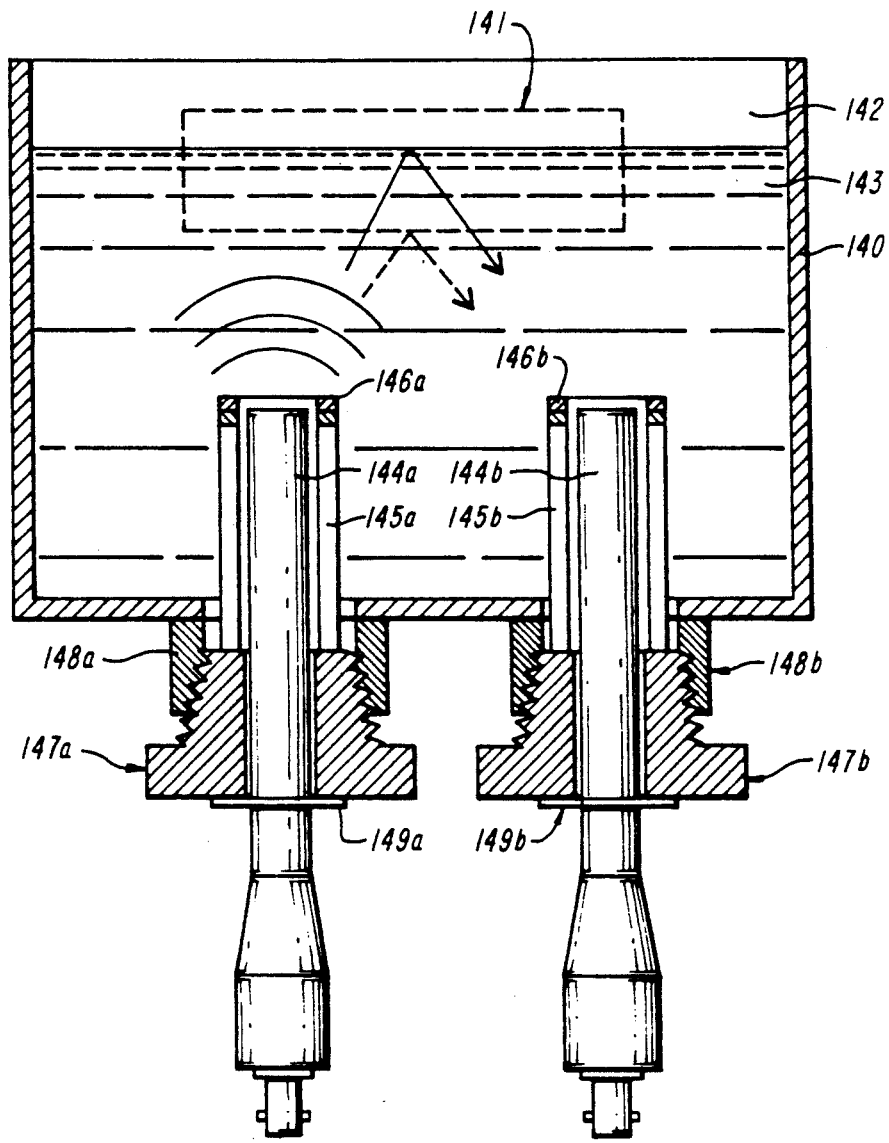
FIG. 14 is a schematic diagram of apparatus for detection of a liquid/vapor interface or a solid/liquid interface.

FIG. 14 depicts another practice of the invention, for ranging and detection of a liquid/vapor interface or a solid/liquid interface. Container 140 is shown enclosing solid 141 which is depicted as partially bounded by an air, gas or vapor mixture 142 and by liquid 143. The broad radiation pattern generated by the embodiment of FIG. 14 permits the waveguides 144A and 144B to be oriented in parallel while communicating over folded acoustic paths. To avoid liquid-borne crosstalk, shields such as dewars 145A and 145B or other highly-reflective shields can be employed. Chamber-borne crosstalk can be reduced or eliminated in a known manner by breaking up the direct acoustic path by threaded or gasket-sealed connections shown at 146A and 146B. Waveguides of the type depicted in FIG. 14 may be mounted to container 140 via threaded mounted plugs 147A and 147B and coupling parts 148A and 148B. Additionally, diaphragms 149A and 149B are utilized between waveguides 144A and 144B, and their corresponding mounting plugs 147A and 147B. Diaphragms 149A and 149B are chosen so that a large acoustic impedance mismatch exists between the diaphragms and the waveguides, and between the diaphragms and the mounting plugs.

If the liquid 143 indicated in FIG. 14 is a molten material at high temperature, such as molten silicon, the waveguides 144A and 144B and other wetted parts should be coated or constructed from materials which are wetted by, but which do not dissolve in the molten material. For example, fused silica waveguide can be suitable for use with molten silicon. Additionally, in certain solidification studies or processes, solidification proceeds from the bottom of the crucible up towards the top. In such cases the waveguides can be mounted above the melt. Examples of other melts and preferred waveguide materials include molten glass in conjunction with molybdenum waveguides, molten aluminum with titanium waveguides (see e.g., Mansfield, U.S. Pat. No. 4,261,197, Apr. 14, 1981), and molten sodium with stainless steel waveguides. Expendable protective waveguide coatings such as gold can be useful in preventing waveguide oxidation prior to immersion. The gold dissolves upon immersion, exposing a clean substrate that is readily wetted by the molten material, as described in the literature. See e.g., Day and Smith, "Under-Sodium Viewing," pp. 191-194 in 1973 *Ultrasonics Symp. Proc.*, IEEE 1973.

As discussed above, because attenuation in substantially all elastic waveguides increases at high temperature and at high frequency, (MHz), low-frequency (KHz) extensional waves offer the advantage of enhanced signal strength over high frequency longitudinal waves. Another advantage of selecting low-frequency extensional waves is that they readily diffract around small holes or indentations in the waveguide. This behavior enables the introduction of pivot points or pivot axles having axes perpendicular to the longitudinal axis of the waveguide, to accommodate cases where the waveguide must periodically be rotated from a "rest" or "retracted" position to a "deployed" position. In the case of a waveguide using magnetostrictive transducers, this movement provides an opportunity to have a movable transducer —such as a Remendur stub—move in or out of a fixed coil. In particular, the transducer can move even while the electrical lead wires remain fixed.

Figure 15:
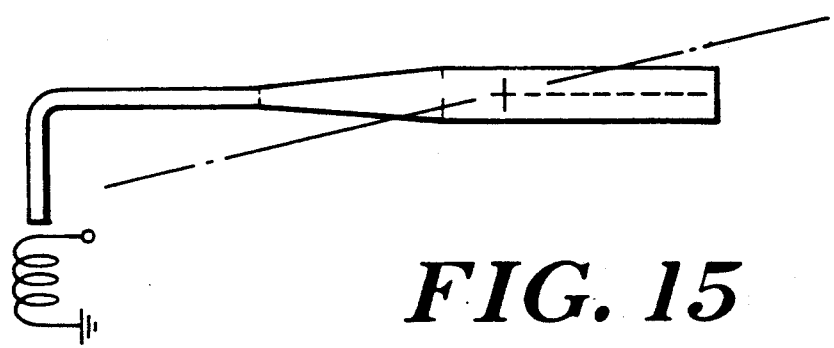
FIG. 15 depicts a waveguide having a pivotal axle perpendicular to the longitudinal axis of the waveguide.

FIG. 15 depicts such a waveguide 150 having a pivotal axle perpendicular to the longitudinal axis 151 of waveguide 150. The pivot point is shown at 152 and a fixed electrical coil is shown at 153.

Figure 16:
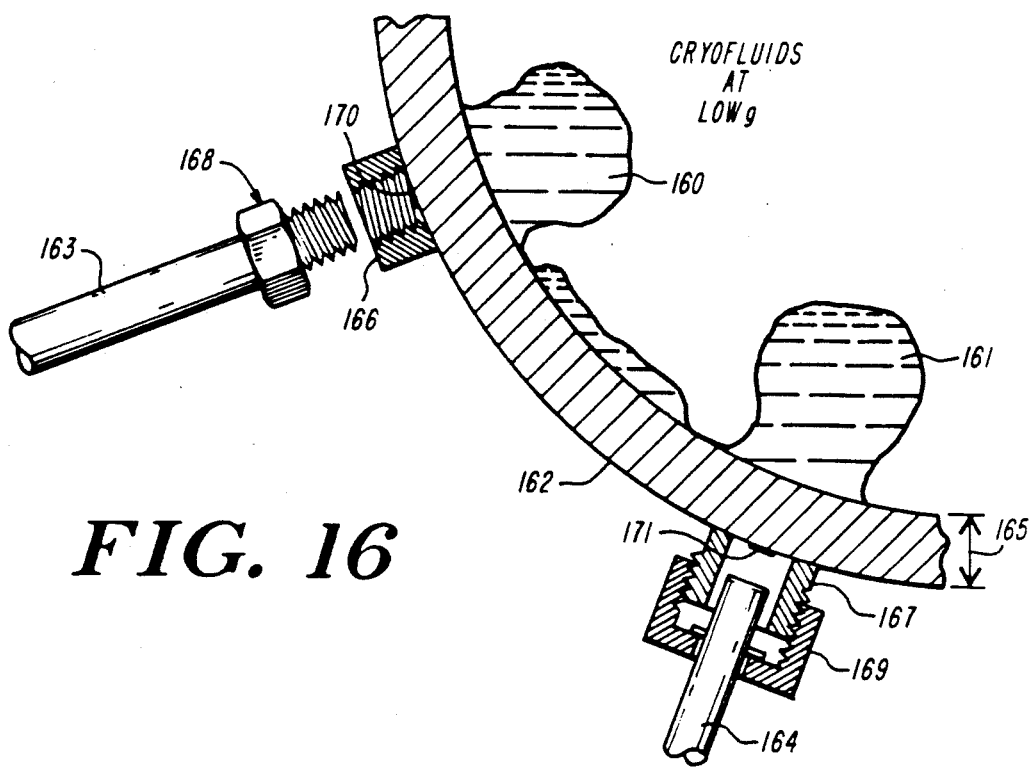
FIG. 16 is a schematic diagram of selectively dispersive waveguides, constructed in accordance with the invention, for a cryogenic tank gaging application.

In the embodiment depicted in FIG. 16, marginally dispersive waveguides are utilized in a low-g cryogenic tank gauging application. The presence or absence of liquid 160 and 161 inside the tank 162 is sensed in response to changes in wall ringdown or changes in transmission from a first sensor 163 to another sensor 164. This detection method relies upon differences in leakage into the internal fluid according to the acoustic impedance of that fluid, as in the impedance difference between liquid and vapor, or relies on the change in phase velocity in the tank wall as a function of liquid loading for flexural waves. For a liquid puddle 160 or 161 the loading depends on the thickness and extent of the puddle as well as on liquid properties, wall thickness 165 and elastic properties, and frequency.

In many cryogenic applications, thermal considerations suggest that it may be advantageous to limit waveguide diameter and use a waveguide material of low thermal conductivity $K_{th}$. Otherwise, heat conducted into the tank along the waveguide may boil liquid away from the wall, perturbing the measurand. However, if boiling can be induced locally, the noise generated by boiling may provide a useful indicator of the presence of liquid. In this latter mode, waveguides 163 and 164 function as thermal sources and passive acoustic receivers. In FIG. 16, the threaded parts 166 and 167 when used in conjunction with mounting plug 168 and pipe coupling part 169 respectively, provide alternate methods for pressure coupling and securing waveguides 163 and 164 against the tank 162. Coupling may be enhanced by a thin layer of Teflon, gold foil, polyimide, or other resilient or non-brittle material shown at 170 and 171 between the waveguide and the tank. However, the number of materials that are sufficiently resilient at cryogenic temperatures is limited. In certain cases, liquid nitrogen or other inert liquid can be employed as the couplant.

Figure 17:
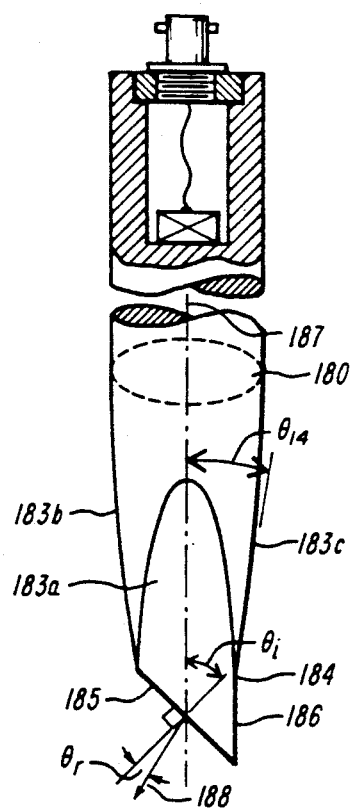
FIGS. 17, 18, and 19 depict alternative embodiments of marginally dispersive waveguides.
Figure 18:
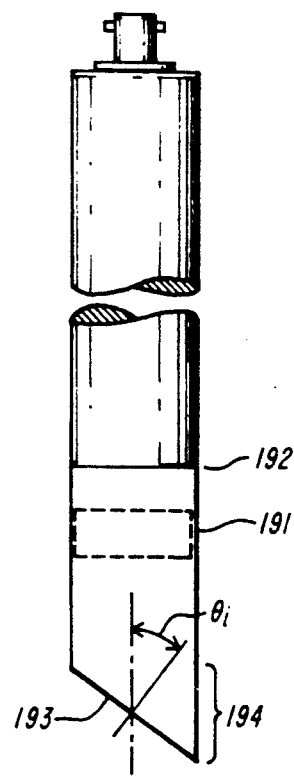
Figure 19:
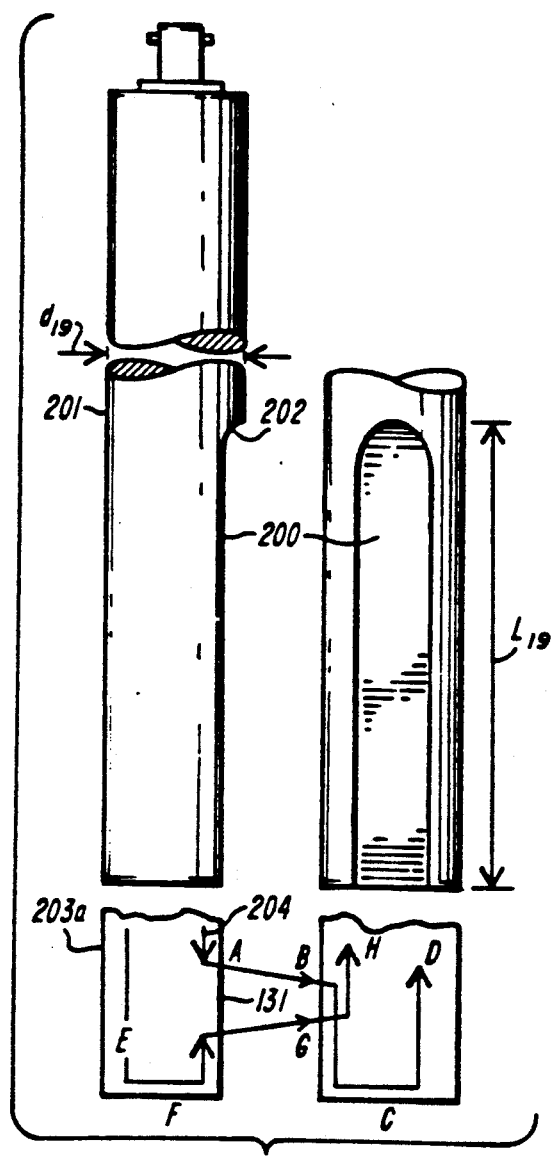

FIGS. 17, 18, and 19 show alternative forms of marginally dispersive buffers designed to transmit or communicate over fluid paths substantially perpendicular to the longitudinal axis of the buffers, or over a region between a pair of substantially Parallel buffers. All references to diameters in FIGS. 17, 18, and 19 correspond to the maximum cross-sectional width existing directly preceding any tapering or chamfering occurring at the radiating end of the illustrated waveguides. The referenced diameters are comparable to the cross-sectional diameters along length $L_c$ previously discussed in relation to FIGS. 3 and 6.

FIG. 17 depicts a cylindrical waveguide of circular cross section 180 containing a cavity 181 at one end, for housing piezoelectric transducer 182. In an embodiment utilizing stainless steel as the waveguide material, circular cross-section 180 can have diameter $d_{17}$ equal to approximately 19 millimeters, for use at 100 kHz. This circular cross-section 180 can be transformed by tapered faces 183A, B and C to a square cross section at plane 184. The end segment can be truncated at $\Theta_i$ equal to 45° by plane 185, so that axial rays are reflected therefrom, and radiate substantially perpendicular to face 186 —i.e., parallel to the longitudinal axis 187. Thus, for example, the tapered faces may form an angle $\Theta_{14}$ of approximately 6 degrees with axis 187 if the length of the faces is approximately 25 millimeters, and $d_{17}$ is 19 millimeters, and the edges of the square at plane 184 just fit within circular cross section 180.

The embodiment shown in FIG. 18 is similar to that of FIG. 17, except that instead of the gradual or tapered transition from round cross section 190 to square cross section 191, an abrupt transition occurs at plane 192. Axial rays striking face 193, which is angled at $\Theta_i$ equal to 45 degrees, generally emanate from face 194. The ratio of extensional wave impedances across the transition plane 192 is approximately $$A_{191}/A_{190} = 4d^2/\pi d^2 = 4/\pi$$

where d is the diameter of circular section 190, which is equal to the edge dimension of the "circumscribed square" section 191. The small reflection at plane 192 can be used as a reference echo when portion 191 is used as a sensor, as in a temperature sensor application. The pressure reflection coefficient $R_{192}$ at plane 192 is essentially given by $$(A_{191}/A_{190} - 1)/(A_{191}/A_{190} + 1)$$

or slightly more than 0.1 for the circle/circumscribed square case.

The embodiment depicted in FIG. 19 utilizes radiation from a flat face 200 whose length $L_{19}$ in the longitudinal direction is greater than the diameter $d_{19}$ by a factor of 3 or more. As a result, extensional energy propagating longitudinally along waveguide 201 leaks off not only at a local region (such as 194 in FIG. 18) but rather over most or all of face 200. The transition to a flat face section may be abrupt or gradual. By way of example, a transition radius 202 is illustrated in FIG. 19. This radius can be less than, equal to or greater than $d_{19}$. Below the front and side views of rod 201 in FIG. 19 is shown a ray diagram for a pair of parallel rods 203A and 203B, each of which is like rod 201 above, and deployed symmetrically. Examples of isoacoustic paths are indicated by ray 204, which follows path ABCD, and ray 205, which follows path EFGH. If rays 204 and 205 are launched simultaneously, rays D and H are "in phase" and would arrive simultaneously at the receiving transducer in the example shown.

While certain cross sections are indicated as circular in the accompanying drawings, those skilled in the art will appreciate that the waveguides need not be of uniform cross section, and need not remain straight or solid. Tubular sections, for example, may be expected to leak more "efficiently" since energy is concentrated in their surface. As a result, higher intensities may be observed in the adjacent fluid.

Moreover, in the embodiments illustrated in FIGS. 17 and 18, the angle of incidence $\Theta_i$ at the beveled ends 185 and 193, respectively, can be 45 degrees, or can be an angle other than 45 degrees, depending in part on the sound speed in the adjacent fluid and on the angle along which radiation is to be preferentially directed. If the adjacent fluid is air at room temperature, for example, having a sound speed c at about 343 m/s (much lower than that of a solid stainless steel rod) radiation at $\Theta_r$ is within a few degrees of the normal:

$$\Theta_r = 0.707 \sin^{-1}(343/5000) = 3.9°$$

if $\Theta_i = 45°$. For the case $d_{17} = 19$ mm, the width of face 185 is also 19 millimeters at $\Theta_i = 45°$, and so, with respect to radiation into air, $$d_{17}/\lambda_{air} = 19/3.43 = 5.5$$

and the width of the main lobe is approximately (1/5.5) radians or 10.3° at f= 100 kHz. Thus, the beveled waveguide radiates at its tip in a direction generally perpendicular to face 186, and also radiates along the oblique path 188. Radiation from regions other than the selected regions can be blocked by alternating impedance-mismatch elements, as discussed above, and repeated as necessary to achieve the desired degree of isolation or blockage.

By adjusting $\Theta_i$ from zero to 45° or larger, up to about 60°, a wide range of refracted angles are possible. Energy can also be radiated in a generally sideways direction, if not blocked, depending upon the selected side geometry and sound speed ratio.

Figure 20:
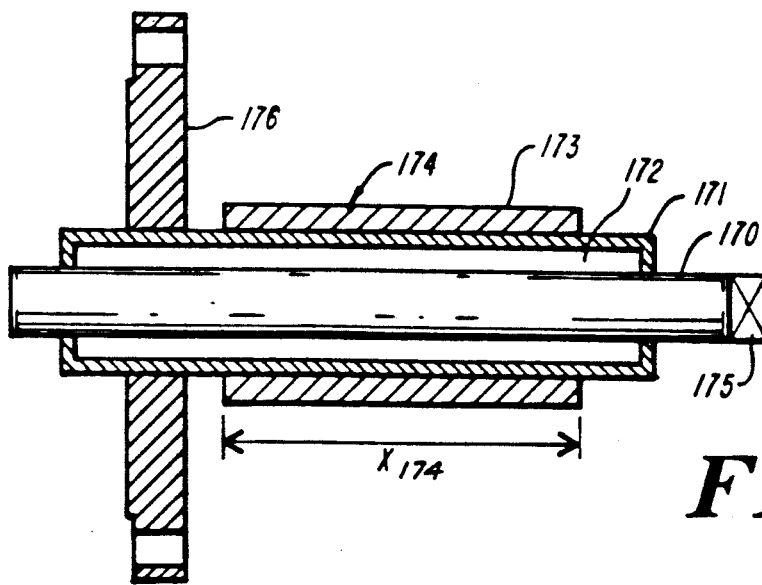
FIG. 20 depicts a marginally dispersive waveguide according to the invention utilizing an evacuated jacket.

FIG. 20 depicts a waveguide 170 partly surrounded by an evacuated jacket 171 so that region 172 is essentially a vacuum region. A second jacket 173 can contain damping material 174 over a length $X_{174}$ so that ultrasonic waves generated by piezoelectric transducer 175 are substantially attenuated before reaching the flange 176. When the assembly in FIG. 20 is used as a receiver, undesired waves entering via the flange are similarly attenuated by damping material 174 before reaching the transducer 175. A certain component of undesired energy, however, has an alternate route over the undamped portion of jacket 171 and can enter the end of rod 170 opposite the transducer 175 where jacket 171 is welded to waveguide 170. This problem can be avoided as shown in FIG. 21.

Figure 21:
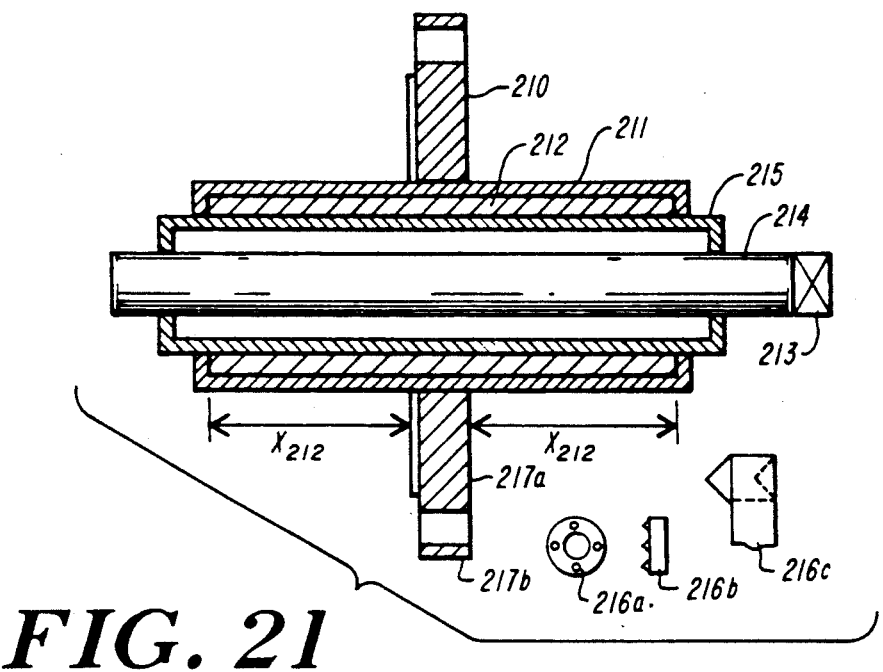
FIG. 21 shows a waveguide assembly utilizing a jacket coated or filled with damping material.

In FIG. 21 the flange 210 is mounted on a jacket 211 partly coated or entirely filled with damping material 212 such that damping over distances $X_{212A}$ and $X_{212B}$ substantially attenuates undesired sound waves on the solid path between the flange 210 and transducer 213 mounted at the end of waveguide 214. Again, vacuum jacket 215 provides thermal and some acoustic isolation, and serves also as a support for the damping jacket 211. As indicated in FIG. 21, these jackets can be welded to one another, the vacuum jacket can be welded to the rod, and a flange can be welded to the damping jacket. Other attachment elements can be utilized, including compression fittings, threads, or brazing.

Also shown in FIG. 21 is a special washer 216A–216C designed to acoustically isolate bolt heads and nuts that would tighten the flange 210 to its mating flange on a vessel or pipe. Flange 210 has small depressions 217A, 217B, . . . , which can correspond to raised areas on washer 216, such as the small conical region 218. As can be seen at 216C, the washer 216 also includes depressions 219 to provide alignment of the adjacent washer. Ordinarily, several washers will be required to achieve a high degree of acoustical isolation. The number of washers required depends in part on the frequency. In general, as frequency decreases, more washers are required for a selected degree of isolation.

The points and depressions in the illustrated flange and washer elements serve to minimize the area of contact between adjacent members, thereby attenuating undesired transmission over such paths. While it is known in the prior art that small contact areas—such as those provided by knife edges—reduce transmission, in the illustrated embodiments, since the bolts and nuts will often be tightened securely for a leak-tight seal, sharp point contacts would be deformed. Therefore, the isolation that knife edges would have provided at modest contact force is reduced as tightening proceeds. Accordingly, the illustrated embodiments utilize a multiplicity of elements, each providing small contact area. While the contact areas are not necessarily small enough to achieve the desired acoustic isolation alone, their isolation effect is cumulative when stacked in series with a number of similar elements.

It has been found that washers centerpunched at three points around the annulus can be nested to provide the isolation sought. Care must be exercised to keep water or other couplant from accidentally filling the gaps between washers or other elements that are to be isolated. A rain cover, for example, can be used in outdoor installations. Alignment—including appropriate nesting of flange and washer bumps and depressions—is critical for avoiding undesired contact with bolt sides. Acoustic isolation can also be achieved by utilizing alternating layers of high- and low-impedance materials such as asbestos substitutes or steel. Bolted flanges, for example, may be isolated by placing alternating high- and low-impedance washers under bolt heads and nuts utilized in connection with the flanges. The isolation is enhanced if one or both of the alternating media is highly attenuating. In addition to asbestos-like gasket materials, Teflon and rubber may be useful in this regard, depending on the frequency and temperature of application.

Figure 22A:
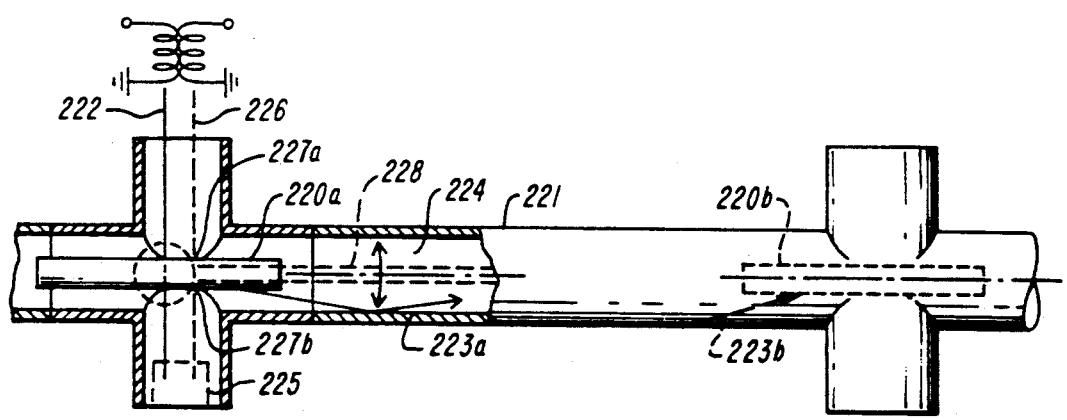
FIG. 22A is a schematic diagram of a flow cell having a pair of marginally dispersive waveguide segments aligned at first and second ends.
Figure 22B:
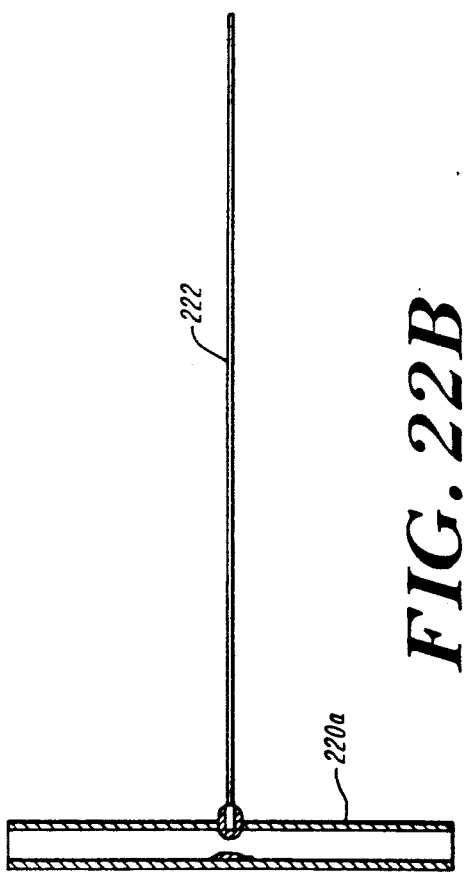
FIG. 22B depicts an embodiment of a waveguide assembly which can be utilized in the flow cell of FIG. 22A.

FIG. 22A depicts a pair of dispersive waveguide segments 220A and 220B aligned at two ends of a flow cell 221. In this embodiment an extensional mode marginally dispersive waveguide 222, which may be magnetostrictive, is silver brazed or welded where it passes through segment 220A at points 229A and 229B. In a preferred embodiment the diameter of the portion of segment 220A that intersects with waveguide 222 is less than $\lambda/4$. This constraint allows element 220A to efficiently mode convert the incoming extensional wave to a flexural wave. The flexural wave leaks off segment 220A along a multitude of rays, including ray 223A. Following multiple folded-path traversals of fluid 224, ray 223A arrives as ray 223B, and generates a flexural wave in 220B.

In an alternate embodiment waveguide 222 contacts but does not pass through segment 220A. Such an embodiment is depicted in the expanded view of FIG. 22B.

To stabilize radiators 220A and 220B, the exciting waveguide 222 can pass through and be secured in a plug 225, shown by dashed lines in 22A to indicate that its use is optional. Another alternative is to introduce an additional stabilizing element 226 that passes through a pair of guide holes 227A and 227B. If stabilizing element 226 is also an extensional mode waveguide, it can be used to generate torsional waves by mode conversion in a coaxial density sensor 228. Such density sensors are generally described in U.S. Pat. No. 4,893,496 of Bau et al.

In connection with the illustrated embodiment, initial experiments demonstrated that water-borne transmission could be readily detected between pairs of dispersive segments 220A and 220B when the frequency was approximately 100 kHz, and the flexural segments were driven at the center of their 100-millimeter length. The segments were constructed from stainless steel, having an outside diameter ranging from approximately 6 to approximately 16 millimeters, and a wall thickness ranging from 0.25 millimeters in a 6 millimeter tube to 1.6 millimeters in larger tubes.

In subsequent experiments, tubular segments 220A and 220B were replaced by strip segments. The strips were constructed of aluminum, and strip dimensions were approximately 6, 9 and 12 millimeters wide, 100 millimeters long and 1.6 millimeters thick. Other low-density materials which may be employed for such strips include titanium, glass, fused silica, graphite, plastic and wood. Those skilled in the art will appreciate that the above-listed dimensional values are provided solely by way of example, and that the invention may be practiced in connection with waveguide elements having dimensions other than those indicated above.

As discussed above, certain prior researchers utilized waveguides consisting of fiber bundles. Conventional fiber bundle waveguides have posed significant technical problems, in part due to the large number of fibers required. For example, in accordance with conventional nondispersive waveguide practice, a waveguide bundle of fiberacoustic stainless steel or Remendur magnetostrictive alloy, having an outside diameter of approximately 25 millimeters, would be employed at 1 MHz for extensional waves having a wavelength of approximately 5 millimeters. Fiber diameters $d_f$ on the order of 0.5 millimeters (0.020 inch) would be utilized—in accordance with the prior art approach—to substantially avoid dispersion. The number of close-packed 0.5-millimeters fibers in a 25-millimeters diameter, substantially cylindrical bundle would be about 1800.

In accordance with the invention, however, by permitting a selected degree of dispersion—i.e., by allowing $d_f$ to increase until the extensional velocity decreases by 10%, the following relationship is attained:

$$\{\pi\sigma a/\lambda\}^2 = 0.1$$

from which $a = 1.5$ millimeters and $d_f = 2a = 3$ mm. The number of close packed dispersive fibers (each of which is about 3 mm diameter) in a 25-millimeters bundle therefore is only about 50, substantially less than 1800 nondispersive fibers.

Figure 23:
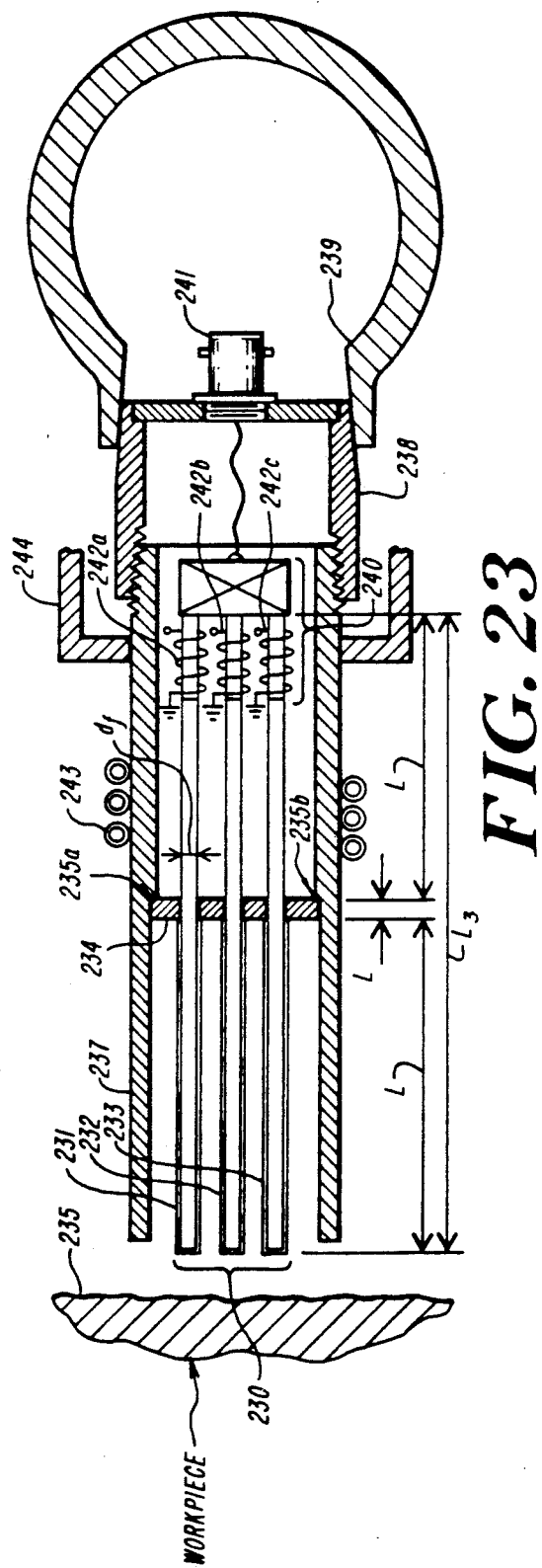
FIG. 23 depicts a waveguide constructed in accordance with the invention from a bundle of marginally dispersive fibers.

FIG. 23 shows a bundle of marginally dispersive fibers. Fifty fibers of 3-millimeters diameter each, may be housed as shown in FIG. 23. The exemplary bundle 230 contains individual marginally dispersive fibers 231, 232, and 233, each passing through holes in a perforated support plate 234 of thickness L. Fiber ends may be rounded slightly to accommodate workpiece irregularities. The width L of support plate 234 is thin compared to wavelength, (if the plate is bonded to the fibers) yet thick enough to withstand pressure or coupling forces The fibers 231-233 may be welded, brazed, or mechanically secured by threading or other means to this plate, so that the radiating end of the bundle can be pressure coupled to an adjacent solid workpiece 235 such as red hot steel, or operated in a fluid at high pressure. Support 234 may be located near the center of the fibers, in which case $L_1$ and $L_2$ would be approximately equal. Support 234 in turn is supported by shoulders 236A and 236B formed on the interior of the shield pipe 237, and may be securely attached thereto, and if necessary sealed to the shield pipe 237, which is capped at one end by threaded cap 238. Cap 238 may be mated with junction box 239.

Electrical connection to the electroacoustic element 240, which may be a flat piezoelectric crystal, is made via connector 241. Another cap (not shown) can be employed to close the shield pipe at the radiating end, in which case the bundle would be attached or coupled to the cap internally. As indicated in FIG. 23, projections on rough-surfaced workpiece 235, when in contact with the bundle, would cause some of the fibers to deform by buckling. This occurs in the region $L_1$, if the inside diameter of the shield pipe 237 is several millimeters larger than the outside diameter of the bundle. The support plate prevents the deformation from reaching the flat end of the bundle where the transducer 240 is attached.

Additionally, cooling coil 243 prevents overheating of the transducer, and fitting 244 supplies the necessary force to couple the bundle 230 to the workpiece 235 or to the fluid under test. If the electroacoustic transducer 240 is magnetostrictive instead of piezoelectric, support plate 234 need not entirely block axial motion when the radiating end accommodates the workpiece surface irregularities. The overall fiber length $L_3$ in FIG. 23 may be about 300 mm. Note that with fiber diameter $d_f$ as large as 3 mm, reasonably high coupling pressure may be developed.

One application of the waveguide depicted in FIG. 23 is that of measuring the thickness x of red hot steel workpieces, which may be take the form of plate or tubing. In this application, where x can range widely, from 3 millimeters to 60 mm, for example, it may be advantageous to cover the thin part of that range with $a_0$ flexural waves—i.e., lowest-order asymmetric Lamb waves—in the workpiece, and the thick part with longitudinal waves at normal incidence. Accordingly, the probe in FIG. 23 may, for this case, utilize a dual-range transducer 240 consisting of low- and high-frequency sources. For example, the transducer end of the bundle may consist of certain fibers containing magnetostrictive segments encircled by the coils 242A-242C for generating frequencies as low as 20 to 100 kHz, to generate $a_0$ waves in the workpiece. Additionally, the crystal may generate 1 MHz waves for interrogating thicker workpieces with longitudinal waves. The connector 241 may then be a multipin connector that allows selective excitation of particular parts of the multi-element transducer.

Alternatively, a single piezoelectric element can be employed, selected to generate 1 MHz waves in its thickness mode and roughly 100-kHz waves in its radial mode. Conventional electronic signal processing elements can be programmed in accordance with known techniques to utilize the low- or the high-frequency part of the generated spectrum—depending on the values of x—in conjunction with appropriately-placed transducers, as discussed above in connection with low-frequency differentially-spaced $a_0$ receivers. This configuration may also be utilized for conventional thickness gaging at normal incidence at 1 MHz.

Figure 24A:
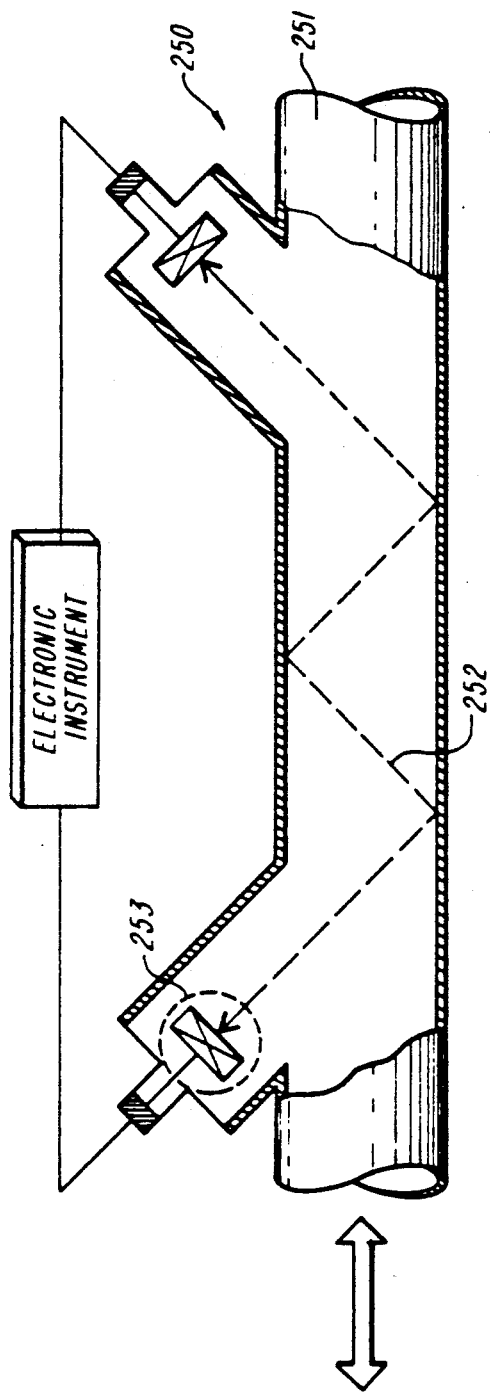
FIGS. 24A and 24B show an ultrasonic flowmeter for cryofluids.
Figure 24B:
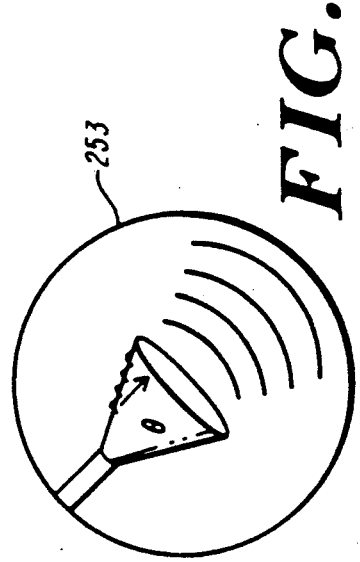

FIG. 24 illustrates that the invention can also be practiced in an embodiment for cryofluid measurement. Depicted at 250 is an example of one form of ultrasonic flowmeter for cryofluids. (Insulation and vacuum jacketing is not shown in FIG. 24.) The cryofluid of interest, including nitrogen vapor, helium vapor, or liquid nitrogen, would be passed through the flowcell 251 and its velocity measured by the contrapropagation method illustrated. To obtain rapid response, on the order of 0.1 second, the alternation of upstream-downstream directions of interrogation shown at 252 should exceed 30 Hz. In practice, an alternation frequency of about 50 to 100 Hz would be employed. The illustrated embodiment can utilize a conical radiator design 253 for flexural mode radiation. Experiments have demonstrated that the lowest-order asymmetric Lamb waves—i.e., $a_0$ flexural waves—at a frequency near 100 kHz can be efficiently generated in thin metal sheets such as aluminum, stainless steel, or titanium. Again, the phase velocity of the $a_0$ wave in such sheets equals a constant times the square root of the frequency-thickness (hereinafter referred to as f*d) product. This square root relationship would be exploited in the conical radiator design as follows. By selecting frequency or sheet thickness, an arbitrarily low phase velocity can be produced. Radiation into the adjacent cryofluid is maximized by approximately matching phase velocity to the speed of sound in the cryofluid.

To demonstrate this behavior, for example, in air, for which c = 343 meters/second near room temperature, the cone could be designed so that phase velocity was greater than approximately the speed of sound. The value of $c_f$, for example, could be selected to be 440 m/s. This can be achieved with an aluminum, stainless steel, or titanium sheet of approximately, 0.2 millimeters thickness at a frequency of 100 kHz. The angle $\Theta$ at which ultrasound leaks off the conical sheets is given by Snell's Law:

$$\Theta = \sin^{-1} c/c_f$$

In this example, $\Theta = \sin^{-1}(343/440) = 51$ degrees. Hence, the included cone angle can be formed at 2(90 degrees $-\Theta$) = 78 degrees. As c varies, adjustment of frequency can maintain radiation along the cone axis. Alternatively, a chirp transmission, in which frequency is rapidly varied, can be utilized, and the frequency of maximum transmission along the cone axis additionally could be a measure of c. Since phase velocity of the $a_0$ flexural wave can be controlled by selecting the f*d product, it is possible to achieve acoustical isolation through a thin-walled delay line.

Figure 25:
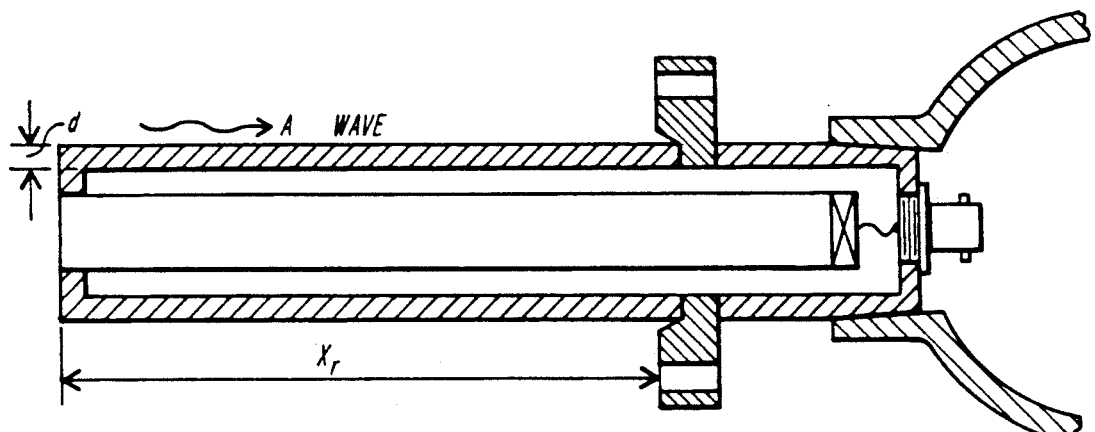
FIG. 25 depicts a slow wave isolator utilizing the $a_0$ flexural wave.

FIG. 25, depicts an example of a slow wave isolator. If d = 0.5 millimeters and frequency f of sound wave A is 50 kHz, then f*d is equal to 0.025 MHz·mm. In steel or aluminum, phase velocity would then be only about 500 meters/second. Accordingly, the delay $t_d$ over the distance $x_r$ would be $$t_d = x_r/c_f = 2 \text{ ms/m}$$

In an 8-inch diameter duct, the 45° flow interrogation path length P is given by $$P = 8(2)^{0.5} = 11.2 \text{ inches}$$

Taking c in cold $H_2$ vapor to be about 500 m/s, it can be seen that if $x_r$ is greater than or equal to approximately P/2, then there should be no acoustic short circuit attributable to the $a_0$ wave. Structure-borne noise must be prevented from propagating at higher velocity plate modes such as $s_0$, and $a_1$.

Figure 26A:
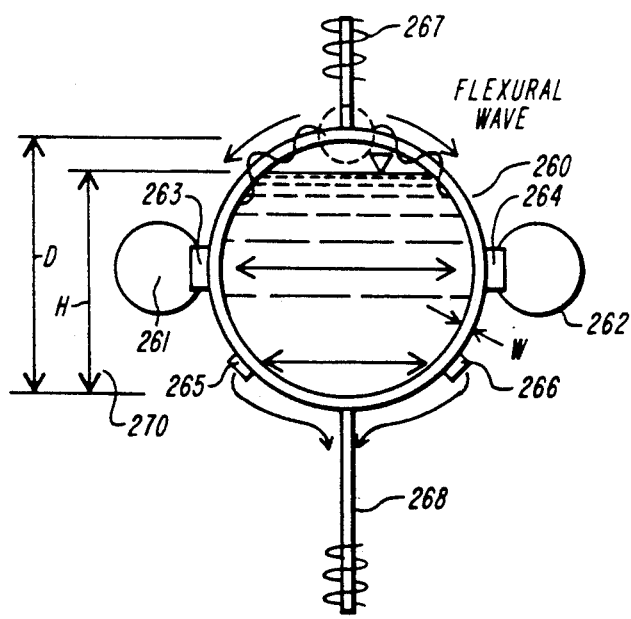
FIG. 26A is an end view of a flowmeter duct employing a slow wave isolator like that depicted in FIG. 25.
Figure 26B:
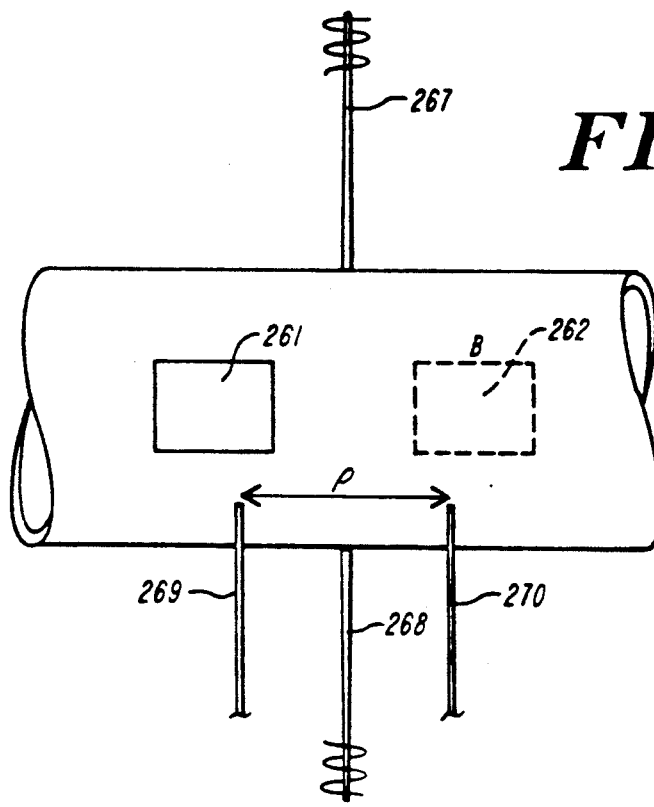
FIG. 26B depicts a side view of the flowmeter duct shown in FIG. 26A for measuring fluid height, density, and flow velocity along a tilted diameter or other tilted chord path.

FIGS. 26A and 26B illustrate how marginally dispersive waveguide receivers may be used in conjunction with flexural or longitudinal mode marginally dispersive waveguide transmitters, to measure fluid height (H), fluid density ($\rho$) and flowmeter velocity (V) along a tilted diameter (D) or other tilted chord path. Volumetric and mass flow rates can also be computed by known techniques from wave transit times obtained using such apparatus.

FIG. 26A is an end view of flowmeter duct 260. Longitudinal mode waveguides 261 and 262 are mounted to duct 260 at opposite ends of diameter $D_1$ via mounting shoes 263 and 264. As can be seen from the side view of FIG. 26B, waveguides 261 and 262 (shown in phantom) are offset from each other along flowmeter longitudinal axis 271. In an alternate embodiment waveguides 261 and 262 may be mounted at opposite ends of chord $C_1$ via mounting shoes 265 and 266. In one embodiment of the invention depicted in FIGS. 26A and 26B, waveguides 261 and 262 may be of the clamp-on variety such as referred to in FIGS. 28A-28C and FIGS. 33A and 33B.

The difference between the transit time for longitudinal waves travelling from waveguide 261 to waveguide 262 and the transit time of waves travelling from waveguide 262 to waveguide 261 may be measured. Using this differential, flowmeter velocity (V) may be calculated. By measuring longitudinal wave transit time along additional tilted chord paths, a flow velocity profile for the duct may also be calculated.

Also shown in FIGS. 26A and 26B are flexural mode marginally dispersive waveguides 267 and 268. Waveguides 267 and 268 are mounted to flow duct 260 so that their longitudinal axes are perpendicular to the surface 272 of fluid 273. Since flexural waves travel more slowly over the region of the flow duct which contains fluid, the flexure wave transit time $t_{flex}1$ between waveguides 267 and 268 is dependent on fluid height (H). Transit time $t_{flex}1$ is also dependent on the density ($\rho$) of the fluid contained within the flow duct. Therefore, to calculate fluid height (H), fluid density ($\rho$) must also be measured.

Flexural mode waveguides 269 and 270 are mounted in such a way as to always be positioned below fluid height (H), thereby causing flexural wave transit time $t_{flex}2$ between waveguides 269 and 270 to be indicative of fluid density ($\rho$). Therefore, $t_{flex}1$ and $t_{flex}2$ may be combined in a known manner to calculate fluid height (H).

Typically, the end view (not shown) of waveguides 267-270 may be flat, chisel-shaped, or cross-shaped, depending in part on heat transfer objectives, and desired radiation pattern.

Figure 27:
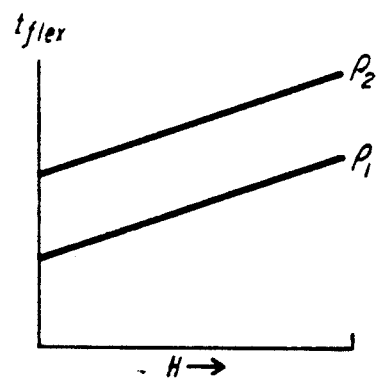
FIG. 27 is a graph depicting flexural wave transit time as a function of fluid height and density.

FIG. 27 is a graph showing flexural wave transit time ($t_{flex}1$) plotted as a function of fluid height (H) for two different fluid densities ($\rho_1$) and ($\rho_2$). As can be observed, $t_{flex}1$ increases as H and $\rho$ increase.

Figure 28A:
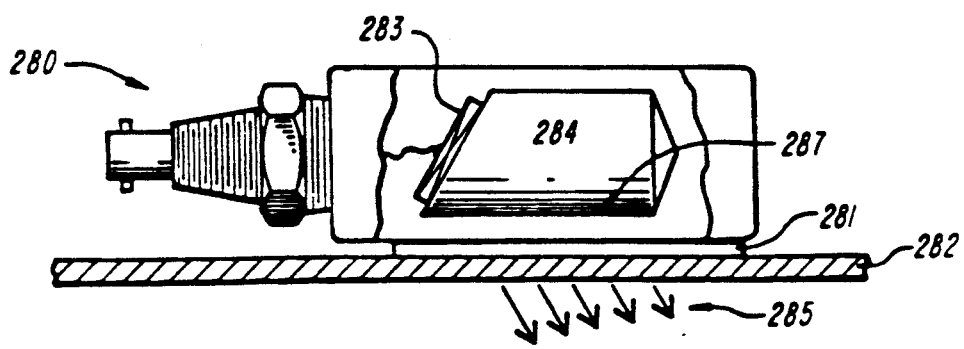

A further embodiment of the invention for measurement of fluid flow and other parameters in a fluid-filled pipe, is depicted in FIGS. 28A-28C. The illustrated configuration utilizes a transducer assembly 280 having a contoured shoe element 281, which provides a selected contact region between transducer assembly 280 and pipe 282, and which has a shoe thickness Y, in the measurement plane, which is equal to a selected constant minus pipe wall thickness W. The measurement plane can be a plane parallel to a diameter of the pipe, or can be a plane corresponding to a tilted chord. The term "thickness," as utilized in connection with this embodiment, therefore refers to distance along the measurement plane. By maintaining constant thickness, it is easier to preserve waveforms even when W changes. In particular, one can create a value of (W+Y) such that f*(W+Y)≡9 MHz·mm, for which the phase velocity of the $a_o$ wave essentially equals a constant (the Rayleigh velocity), thereby avoiding dispersion for the $a_o$ wave. Even for smaller f*(W+Y) products a constant phase velocity is predicted at f=constant when (W+Y)=constant, for a given pipe material, e.g., steel.

In operation, acoustic energy 285 generated by conventional transducer 283 is transmitted through waveguide 284 and shoe 281 into pipe 282 containing liquid 286. The shoe 281 can be constructed from stainless steel SS303, 304 or 316, or a similar material, having density and sound speeds similar to those of the conduit with which the shoe 281 is to be used. The shoe 281 can be coupled to the pipe 282 utilizing epoxy, a thin RTV layer, or grease. As indicated in FIG. 28C, shoe element 281 includes a contoured face 286, for providing selected contact with pipe 282. Face 288 can, for example, have a constant radius R equal to one-half the outside diameter of the pipe 282. Alternatively, R can be less than or greater than one-half the outside diameter of the pipe 282, and the shoe 281 can be contoured to provide a selected area or line of contact with the workpiece. The longitudinal axis of the waveguide 284 is parallel to the longitudinal axis of pipe 282, such that the ultrasonic waves are coupled into the specimen from a longitudinal side 287.

FIG. 29 is a table of shoe dimensions R and Y which can be utilized for selected pipe sizes. In a preferred embodiment of the invention, shoe thickness Y is calculated as a function of pipe wall thickness W, to provide a total thickness in the measurement plane of $W+Y$ equal to a selected constant. As indicated in the table set forth in FIG. 29, this constant total thickness can be, for example, 0.375 inches for schedule 40 pipe, and 0.5 inches for schedule 120 pipe.

Figure 30:
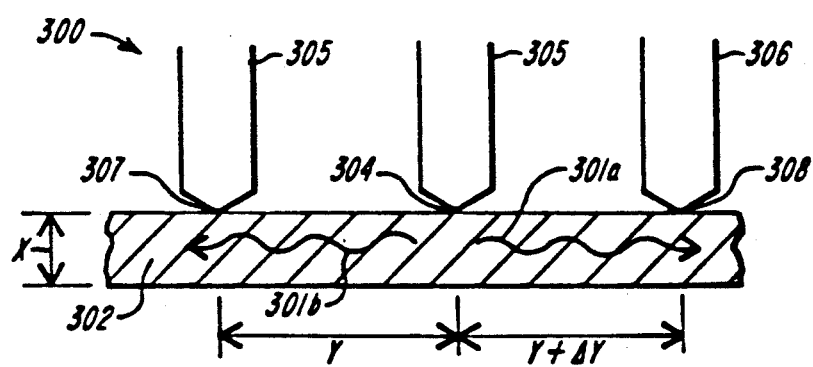
FIG. 30 is a schematic diagram depicting an ultrasonic measurement configuration for thickness gauging of red-hot steel.

FIG. 30 depicts another embodiment of the invention, adapted for measuring the thickness X of red-hot steel sheet or tubing. In accordance with the invention, the apparatus 300 depicted in FIG. 30 provides measurement of thickness X based upon the relationship of thickness to phase velocity $c_f$ of flexural waves at frequencies on the order of 100 kHz.

In the configuration shown in FIG. 30, flexural waves 301A and 301B are launched in the workpiece 302 by the transmitting extensional mode marginally dispersive waveguide 303, which couples a conventional ultrasonic transducer (not shown) to a selected contact point or region 304 on the workpiece 302. Receiving waveguides 305 and 306 contact the workpiece 302 at points or regions 307 and 308, which are displaced from point 304 by distances Y and $Y+dY$, respectively. Flexural waves 301A and 301B propagating through the workpiece 302 are received by waveguides 305 and 306, and propagation times are determined to provide a measure of phase velocity $c_f$, and thus thickness X. Differential timing circuitry utilized in connection with this embodiment can be checked for zero offset by measuring transit times in opposite (contra-propagating) directions between adjacent or non-adjacent pairs of waveguides.

Figure 31:
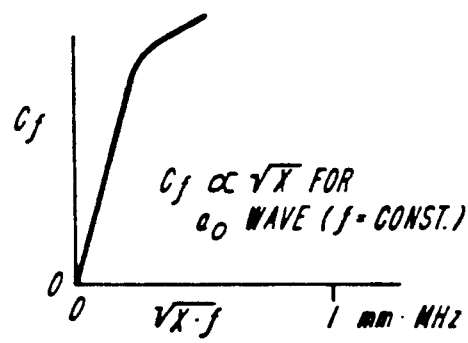
FIG. 31 is a graph depicting phase velocity as a function of the frequency-thickness product for the embodiment of FIG. 30.

FIG. 31 illustrates the relationship of $c_f$ to X. As indicated therein, for the $a_0$ wave, when frequency is held constant, phase velocity $c_f$ is proportional to the square root of thickness.

Figure 32:
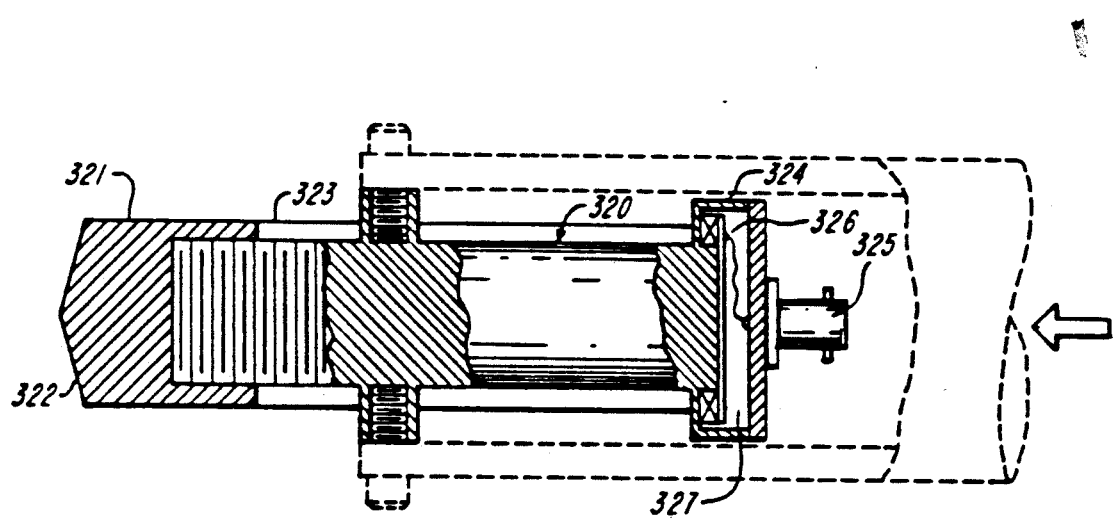
FIG. 32 depicts a marginally dispersive waveguide which can be utilized in the embodiment of FIGS. 30 and 31, having a replaceable tip for thickness gaging of red hot steel sheet or tubing.

FIG. 32 depicts a marginally dispersive waveguide 320 which can be utilized in the embodiment of FIGS. 30 and 31 for thickness gaging of high temperature materials. The embodiment depicted in FIG. 32 is especially advantageous in thickness gaging of rough or red-hot steel sheet or tubing. Waveguide 320 preferably includes a replaceable contact element 321, which can have a chisel tip 322 for contact with a high temperature workpiece, and a shaft 323, through which coupling force can be applied to the tip 322. The shaft 323 can be constructed, for example, from stainless steel, having a 19 millimeter diameter and 100 millimeter length. These specifications are provided by way of example, and other materials and dimensions may be employed.

Waveguide 320 can also include a low-frequency hoop mode piezoelectric transducer crystal 324 for conversion of electrical excitations to ultrasonic energy in the transmission mode, or for converting ultrasound to electrical signals in the receiving mode. The piezoelectric crystal 324 can be coupled to a conventional BNC electrical connector 325 via electrical lead 326. Damping elements 327, which can include asbestos substitutes or other damping materials discussed above, can be incorporated into the waveguide in certain applications to achieve a selected level of acoustic damping.

Figure 33A:
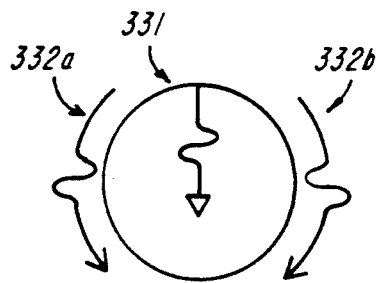
FIGS. 33A and 33B depict a portion of a flexural mode clamp-on flowmeter for fluid-carrying pipes.
Figure 33B:
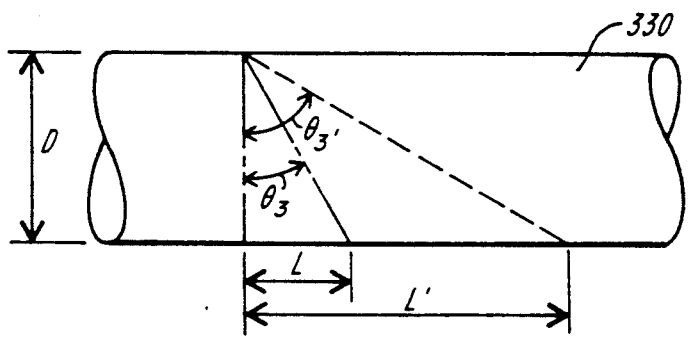

FIGS. 33A and 33B depict a portion of a clamp-on flowmeter constructed in accordance with the invention, which provides improved accuracy and reduced cost as follows. As will be apparent from the preceding discussion, the phase velocity in the wall of the pipe 330 can be controlled by selecting the frequency of the interrogating waves. For any given pipe wall thickness d, there is a frequency that yields an arbitrarily low $c_f$. Ordinarily, the shear or longitudinal wave speed in the pipe wall, usually aluminum, is larger than the speed of sound in water by a factor of 2 or 4, respectively. This has two consequences: acoustic short circuit noise, shown at 331 is a potential problem, and the refracted angle $\Theta_3$ in the water is limited to undesirably small values, typically less than 30 degrees.

However, when f is selected to be low enough so that, for example, $$c_f = 1.1 c_L$$

where $c_L$ = longitudinal velocity in water (1500 m/s), then the short circuit can be delayed, and $\Theta_3$ can be increased substantially to $\Theta'_3$. The short circuit is delayed behind the waterborne signal because the circumferential path indicated at 332A and 332B is approximately $\pi/2$ times longer than the diameter path 333. The ratio of short circuit time $t_{sc}$ to longitudinal mode water time $t_L$ is, for the present "end view" example, $$\pi c_L / 2 c_f = 1.43$$

Tables of elliptic integrals may be used for more exact calculations of transit time ratios for tilted-diameter fluid paths and elliptical short-circuit paths. The end result is that it is possible to delay the "short circuit" so that, for sufficiently low $c_f$, $t_{sc}$ exceeds $t_L$, as desired here.

The refracted angle $\Theta_3$ is calculated from Snell's Law to be $$\Theta_3 = \sin^{-1} 0.909 = 65 \text{ degrees}$$

The increase in sensitivity to flow is given by the ratio of axially-projected interrogation path lengths $L_f/L_0$, where $L = D \tan \Theta_3$. Taking $L_0$ as the path for $\Theta_3 = 27$ degrees, the ratio of the lengths is $$[\tan 65 \text{ degrees}]/[\tan 27 \text{ degrees}] = 4.28$$

The selection of low frequency means that the fluid would be interrogated at a longer wavelength, which will be less sensitive to blockage by bubbles, such as pump-induced cavitation bubbles.

An ultrasonic measurement system configured for operating in the marginally dispersive region depicted in FIG. 1 can include elements for acoustically isolating the waveguides. Acoustic isolation is preferred because low frequency waves such as the 100 kHz waves typically utilized in such systems tend to leak around the container or support structure of the transducer assemblies.

Figure 34:
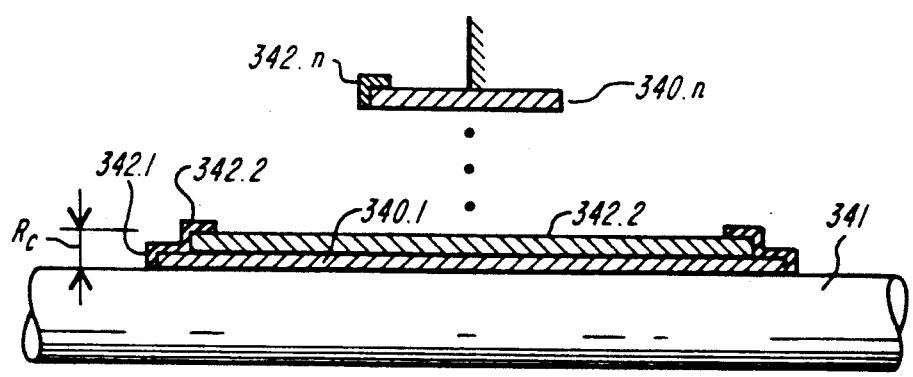
FIG. 34 is a schematic diagram depicting acoustic isolation by means of multiple noise splitting stages.

FIG. 34, accordingly shows a preferred embodiment of the invention which utilizes a multiple stage noise splitting configuration. As depicted in the sectional view of FIG. 34, the acoustic isolation can be provided by dampened concentric tubes 340.1, 340.2, . . . , 340.n, joined at one or more points to the waveguide 341. Each tube functions as a noise-slitting stage, to dissipate undesired ultrasonic energy. The wall thickness and inter-tube spacing can be varied to suit particular applications. The inter-tube gap can be, for example, 1.5 millimeters.

The tubes can be constructed from materials such as stainless steel, or from highly attenuating materials such as Teflon TM tubing. The concentric tubes can be damped by incorporating ultrasound attenuating materials in the form of inserts 342.1, 342.2, . . . 342.n, into each concentric tube, or by utilizing absorptive coatings. In addition, if the concentric tubes are not constructed from highly attenuating material, noise dampening material can be incorporated between each tube, to further dissipate energy.

FIG. 35 shows the relationship between the number of noise slitting stages and the degree of isolation provided. In particular, the isolation provided by the illustrated configuration is proportional to $(\frac{1}{2})^n$, where n is equal to the number of noise splitting stages. Experiments have generally demonstrated that isolation increases approximately at the theoretically-predicted rate of 3 dB per noise splitting stage.

In addition to the noise slitting stages illustrated in FIGS. 34 and 35, isolation elements utilized in connection with the invention can also include locally threaded sections on which bushings may be mounted for adapting the slender waveguide to a sturdy concentric supporting tube, or for providing a connection to a flange which is acoustically isolated using gasket materials which attenuate ultrasound. As discussed above, bolted flanges may be isolated by alternating high- and low-impedance washer materials.

It will thus be seen that the invention efficiently attains the objects set forth above, among those made apparent from the preceding description. It will be understood that changes may be made in the above construction and in the foregoing sequences of operation without departing from the scope of the invention. It is accordingly intended that all matter contained in the above description or shown in the accompanying drawings be interpreted as illustrative rather than in a limiting sense.

It is also to be understood that the following claims are intended to cover all of the generic and specific features of the invention as described herein, and all statements of the scope of the invention which, as a matter of language, might be said to fall therebetween.

Having described the invention, what is claimed as new and secured by Letters Patent is:

1. A method for ultrasonically measuring selected physical parameters of a specimen, said method including improvements comprising the steps of
    generating ultrasonic waves having a characteristic wavelength, and
    configuring a marginally dispersive waveguide for transmitting the ultrasonic waves into the specimen in a selectively dispersive manner, the configuring step including the steps of
    selecting waveguide diameters over the length of the waveguide so the phase velocity of the ultrasonic waves in the waveguide, averaged over the entire length of the waveguide, exceeds ninety percent of the square root of the ratio of Young's Modulus to waveguide material density,
    selecting waveguide diameters so that said diameters are less than one wavelength and greater than twenty-five percent of wavelength over substantially the entire length of the marginal dispersive waveguide.

2. The method of claim 1, wherein the configuring step includes the further step of
    selecting waveguide diameter so that, over at least seventy-five percent of the length of the marginally dispersive waveguide the phase velocity of the ultrasonic waves in the waveguide exceeds ninety percent of the square root of the ratio of Young's modulus to density.

3. The method of claim 1, wherein the configuring step includes the further step of
    selecting waveguide diameters so that waveguide deflection due to gravity, over a cantilevered segment of the waveguide, having a supported end, and a radiating end in proximity with the specimen, is less than the largest of said selected diameters.

4. The method of claim 1, wherein the configuring step includes the further step of
    constructing the marginally dispersive waveguide from an acoustic bundle of selectively dispersive fibers.

5. The method of claim 1, wherein the configuring step includes the step of
    constructing the marginally dispersive waveguide from a single acoustically conductive element.

6. The method of claim 1, wherein the configurating step includes the steps of
    constructing the marginally dispersive waveguide from an acoustically conductive element which is hollow along a portion thereof, and
    selecting said diameters along said portion to be outside diameters.

7. The method of claim 1, wherein the configuring step includes the step of
    constructing the marginally dispersive waveguide from an acoustically conductive element which is solid along a selected portion thereof.

8. The method of claim 1, wherein the configuring step includes the further step of
    configuring the marginally dispersive waveguide to have non-circular cross-sections.

9. The method of claim 1, wherein the configuring step includes the further step of
    configuring the marginally dispersive waveguide so that at least two of said diameters are unequal.

10. The method of claim 1, comprising the further steps of
    configuring a support structure to support the marginally dispersive waveguide, and
    acoustically isolating the marginally dispersive waveguide to reduce leakage of acoustic energy around the support structure.

11. The method of claim 1, comprising the further step of
    acoustically coupling longitudinal waves from the waveguide into the specimen.

12. The method of claim 1, comprising the further step of
    acoustically coupling shear waves from the waveguide into the specimen.

13. The method of claim 1, comprising the further step of
    acoustically coupling Rayleigh waves from the waveguide into the specimen.

14. The method of claim 1, comprising the further step of
    acoustically coupling Lamb waves from the waveguide into the specimen.

15. The method of claim 1, wherein the utilizing step includes the step of
    acoustically coupling lowest-order asymmetric waves from the waveguide into the specimen.

16. The method of claim 1, comprising the further steps of
    mode converting compressional waves in the marginally dispersive waveguide into flexural waves, and acoustically coupling the flexural waves from the waveguide into the specimen.

17. The method of claim 1 comprising the further step of
acoustically coupling a selected combination of compressional and flexural waves, having selected wavelengths, from the waveguide into the specimen.

18. The method of claim 1, wherein the utilizing steps includes the step of
launching ultrasonic waves into the specimen from a radiating end of the marginally dispersive waveguide.

19. The method of claim 1, wherein the utilizing step includes the step of
acoustically coupling ultrasonic waves into the specimen from a selected longitudinal side of the marginally dispersive waveguide.

20. The method of claim 1, wherein the utilizing step includes the step of
acoustically coupling ultrasonic waves into a fluid specimen.

21. The method of claim 1, wherein the utilizing step includes the step of
acoustically coupling ultrasonic waves into a solid specimen.

22. The method of claim 1, comprising the further step of acoustically isolating the marginally dispersive waveguide.

23. The method of claim 22, wherein the isolating step includes the step of coupling to the marginally dispersive waveguide a plurality of energy attenuating stages.

24. The method of claim 23, wherein the coupling step includes the step of acoustically damping the plurality of energy attenuating stages.

25. The method of claim 1, comprising the further steps of
coupling a first marginally dispersive waveguide to a first surface region of the specimen at a first site,
coupling a second marginally dispersive waveguide to the first surface region, at a second site spaced apart from the first site,
acoustically coupling the ultrasonic waves from said first waveguide into the specimen and receiving the ultrasonic waves propagating through the specimen at said second waveguide,
measuring time of propagation of said ultrasonic waves from such first site to said second site, said time being indicative of the presence of fluid adjacent to a second surface of the specimen.

26. The method of claim 1, comprising the further steps of
coupling a first marginally dispersive waveguide to a first surface region of the specimen at a first site,
coupling a second marginally dispersive waveguide to the first surface region, at a second site spaced apart from the first site,
acoustically coupling the ultrasonic waves from said first waveguide into the specimen and receiving the ultrasonic waves propagating through the specimen at said second waveguide,
measuring time of propagation of said ultrasonic waves from such first site to said second site, said time being indicative of specimen thickness.

27. The method of claim 1, comprising the further steps of
coupling a first marginally dispersive waveguide to a first surface region of the specimen at a first site,
coupling a second marginally dispersive waveguide to the first surface region, at a second site spaced apart from the first site,
acoustically coupling the ultrasonic waves from said first waveguide into the specimen and receiving the ultrasonic waves propagating through the specimen at said second marginally dispersive waveguide,
adjusting frequency of the lowest-order asymmetric waves so that the waves have a selected phase velocity greater than the longitudinal sound velocity in a fluid adjacent to a second surface of the specimen, and less than 1.4 times the longitudinal velocity in said fluid,
measuring time propagation of said ultrasonic waves from such first site to said second site, said time being indicative of liquid flow adjacent to said second surface of the specimen.

28. The method of claim 1, comprising the further steps of
coupling a first marginally dispersive waveguide to a first surface region of the specimen at a first site,
coupling a second marginally dispersive waveguide to the first surface region at a second site spaced apart from the first site,
selecting the frequency of said ultrasonic waves to be coupled into the specimen so that the propagation time of longitudinal waves through fluid adjacent to a second surface of the specimen is less than flexural wave propagation time through the specimen between the first and second sites,
acoustically coupling said ultrasonic waves from said first waveguide into the specimen and receiving said ultrasonic waves propagating through the specimen at said second waveguide,
measuring said time of propagation of said ultrasonic waves from said first site to said second site, said time being indicative of selected parameters of said fluid.

29. The method of claim 28, comprising the further step of
configuring the marginally dispersive waveguides so that longitudinal wave propagation in the fluid is substantially parallel to the longitudinal axes of the marginally dispersive waveguides.

30. The method of claim 28, wherein said specimen has longitudinal and transverse axes and comprising the further step of
adjusting the coupled ultrasonic wave frequency so that a selected portion of ultrasonic energy radiation is within a selected angle with respect to the longitudinal axis of a portion of the specimen through which said coupled waves are propagating.

31. The method of claim 1, comprising the further step of utilizing a conical sealing surface.

32. The method of claim 1, comprising the further step of utilizing a tapered pipe thread sealing surface.

33. The method of claim 1, wherein the configuring step includes the further step of
configuring the waveguide so that all of said diameters are substantially equal.

34. The method of claim 1, wherein the configuring step includes the further step of configuring the waveguide to have substantially circular cross-sections.

35. In apparatus for ultrasonically measuring selected physical parameters of a specimen, the apparatus comprising means for generating ultrasonic waves having a characteristic wavelength, the improvement comprising marginally dispersive waveguide means for transmitting the ultrasonic waves into the specimen in a selectively dispersive manner, the marginally dispersive waveguide means including a marginally dispersive waveguide constructed from at least one selected material, said waveguide being characterized by a length and selected diameters, said diameters being such that the phase velocity of the ultrasonic waves in the waveguide, averaged over the entire length of the waveguide, exceeds ninety percent of the square root of the ratio of Young's modulus to waveguide material density, each of said diameters being less than approximately one wavelength and greater than approximately twenty-five percent of wavelength over substantially the entire length of the waveguide.

36. Apparatus according to claim 35, wherein the marginally dispersive waveguide is further characterized by a waveguide diameter such that, over at least seventy-five percent of the length of the marginally dispersive waveguide the phase velocity of the ultrasonic waves in the waveguide exceeds ninety percent of the square root of the ratio of Young's modulus to density.

37. Apparatus according to claim 35, wherein the marginally dispersive waveguide is further characterized by waveguide diameters such that waveguide deflection due to gravity, over a cantilevered segment of the waveguide, having a supported end, and a radiating end in proximity with the specimen, is less than the largest of said diameters.

38. Apparatus according to claim 35, wherein the marginally dispersive waveguide includes a plurality of acoustically conductive selectively dispersive fibers.

39. Apparatus according to claim 35, wherein the marginally dispersive waveguide includes a single acoustically conductive element.

40. Apparatus according to claim 35, wherein the marginally dispersive waveguide includes an acoustically conductive element which is hollow along a portion thereof, said diameters along said portion being outside diameters.

41. Apparatus according to claim 35, wherein the marginally dispersive waveguide includes an acoustically conductive element which is solid along a portion thereof.

42. Apparatus according to claim 35, wherein the marginally dispersive waveguide has non-circular cross-sections.

43. Apparatus according to claim 35, wherein at least two of said diameters are equal.

44. Apparatus according to claim 35, further comprising support means for supporting the marginally dispersive waveguide, and isolation means for acoustically isolating the marginally dispersive waveguide to reduce leakage of acoustic energy around the support structure.

45. Apparatus according to claim 35, wherein the marginally dispersive waveguide comprises means for acoustically coupling longitudinal waves from the waveguide into the specimen.

46. Apparatus according to claim 35, wherein the marginally dispersive waveguide comprises means for acoustically coupling shear waves from the waveguide into the specimen.

47. Apparatus according to claim 35, wherein the marginally dispersive waveguide further comprises means for acoustically coupling Rayleigh waves from the waveguide into the specimen.

48. Apparatus according to claim 35, wherein the marginally dispersive waveguide further comprises means for acoustically coupling Lamb waves from the waveguide into the specimen.

49. Apparatus according to claim 35, wherein the marginally dispersive waveguide further comprises means for acoustically coupling lowest-order asymmetric waves from the waveguide into the specimen.

50. Apparatus according to claim 35, wherein the waveguide further comprises means for mode converting compressional waves in the marginally dispersive waveguide into flexural waves and means for acoustically coupling said flexural waves from the waveguide into the specimen.

51. Apparatus according to claim 35, further comprising means, coupled to the marginally dispersive waveguide, for acoustically coupling a selected combination of compressional and flexural waves, having selected wavelengths, into the specimen.

52. Apparatus according to claim 35, wherein the waveguide further comprises means for acoustically coupling ultrasonic waves into the specimen from a radiating end of the marginally dispersive waveguide.

53. Apparatus according to claim 35, wherein the waveguide further comprises means for acoustically coupling ultrasonic waves into the specimen from a selected longitudinal side of the marginally dispersive waveguide.

54. Apparatus according to claim 35, wherein the waveguide further comprises means for acoustically coupling ultrasonic waves into a fluid specimen.

55. Apparatus according to claim 35, wherein the waveguide further comprises means for acoustically coupling ultrasonic waves into a solid specimen.

56. Apparatus according to claim 35, further comprising isolation means for acoustically isolating the marginally dispersive waveguide.

57. Apparatus according to claim 56, wherein isolating means includes a plurality of energy attenuating stages coupled to the marginally dispersive waveguide.

58. Apparatus according to claim 57, the plurality of energy attenuating stages are acoustically damped.

59. An apparatus according to claim 35, comprising a first marginally dispersive waveguide coupled to a first surface region of said specimen at a first site, for coupling said ultrasonic waves into the specimen, a second marginally dispersive waveguide, coupled to the first surface region, at a second site spaced apart from the first site, for receiving said ultrasonic waves propagating through the specimen, and measuring means, coupled to the first and second waveguides, for measuring time of propagation of said ultrasonic waves from said first site to said second site, said time being indicative of the presence of fluid adjacent to a second surface of the specimen.

60. An apparatus according to claim 35, comprising
a first marginally dispersive waveguide coupled to a first surface region of the specimen at a first site, for coupling said ultrasonic waves into the specimen, a second marginally dispersive waveguide, coupled to the first surface region, at a second site spaced apart from the first point, for receiving said ultrasonic waves propagating through the specimen, and measuring means, coupled to the first and second waveguides, for measuring time of propagation of said ultrasonic waves from said first site to said second site, said time being indicative of specimen thickness.

61. An apparatus according to claim 35, comprising
a first marginally dispersive waveguide coupled to a first surface region of the specimen at a first site, for coupling said ultrasonic waves into the specimen, a second marginally dispersive waveguide, coupled to the first surface region, at a second site spaced apart from the first point, for receiving said ultrasonic waves propagating through the specimen, adjusting means for adjusting frequency of lowest-order asymmetric waves so that the waves have a selected phase velocity greater than the longitudinal sound velocity in a fluid adjacent to a second surface of the specimen, and less than 1.4 times the longitudinal velocity of the liquid flow, and measuring means, coupled to the first and second waveguides, for measuring time of propagation of said ultrasonic waves from said first site to said second site, said time being indicative of liquid flow adjacent to the second surface of the specimen.

62. An apparatus according to claim 35, wherein said specimen contains fluid, and comprising at least a first marginally dispersive waveguide coupled to a first surface region of the specimen at a first site, for coupling said ultrasonic waves into the specimen, at least a second marginally dispersive waveguide coupled to said first surface region, at a second site spaced apart from the first site, for receiving said ultrasonic waves propagating through the specimen, and means for selecting the frequency of said ultrasonic waves coupled into the specimen so that the propagation time of longitudinal waves through fluid adjacent to a second surface of the specimen between the first and second sites is less than flexural wave propagation time through the specimen between the first and second sites, and measuring means, coupled to the first and second waveguides, for measuring time of propagation of said ultrasonic waves through said fluids from said first site to said second site, said time being indicative of selected parameters of said fluid.

63. Apparatus according to claim 62, wherein
the marginally dispersive waveguides are configured such that longitudinal wave propagation in the fluid is substantially parallel to the longitudinal axes of the marginally dispersive waveguides.

64. Apparatus according to claim 62, further comprising
means for adjusting the coupled ultrasonic wave frequency so that a selected portion of ultrasonic energy radiation is within a selected angle with respect to the longitudinal axis of a portion of the specimen through which said coupled waves are propagating.

65. Apparatus according to claim 35, wherein the marginally dispersive waveguide includes a conical sealing surface.

66. Apparatus according to claim 35, wherein the marginally dispersive waveguide includes a tapered pipe thread sealing surface.

67. An apparatus according to claim 35, wherein said diameters are substantially equal.

68. An apparatus according to claim 35 wherein the waveguide has substantially circular cross-sections.

* * * * *